US008221972B2

(12) United States Patent
Lemaire et al.

(10) Patent No.: US 8,221,972 B2
(45) Date of Patent: Jul. 17, 2012

(54) USE OF CONJUGATES WITH LINKERS CLEAVABLE BY PHOTODISSOCIATION OR FRAGMENTATION FOR MASS SPECTROMETRY ANALYSIS OF TISSUE SECTIONS

(75) Inventors: Rémi Lemaire, Ormesson sur Marne (FR); Isabelle Fournier, Bourghelles (FR); Michel Salzet, Bourghelles (FR); Michel Dechamps, Verviers (BE); Jean-Claude Edmond Tabet, Morangis (FR); Gottfried Proess, Butgenbach (BE); Ivo Rudloff, Essen (DE); Marc Lemaitre, Cincinnati, OH (US)

(73) Assignees: Centre National de la Recherche Scientifique (CNRS), Paris (FR); Universite des Sciences et Technologies de Lille, Villeneuve d'Ascq (FR); Eurogentec S.A., Seraing (FR)

( * ) Notice: Subject to any disclaimer, the term of this patent is extended or adjusted under 35 U.S.C. 154(b) by 1221 days.

(21) Appl. No.: 11/921,678

(22) PCT Filed: Jun. 7, 2006

(86) PCT No.: PCT/IB2006/002309
§ 371 (c)(1),
(2), (4) Date: Dec. 6, 2007

(87) PCT Pub. No.: WO2007/000669
PCT Pub. Date: Jan. 4, 2007

(65) Prior Publication Data
US 2011/0151451 A1    Jun. 23, 2011

Related U.S. Application Data

(60) Provisional application No. 60/687,848, filed on Jun. 7, 2005.

(51) Int. Cl.
*C12Q 1/68* (2006.01)
*C07H 21/00* (2006.01)
*C07H 19/04* (2006.01)
(52) U.S. Cl. ........ 435/6.1; 536/23.1; 536/24.3; 536/26.6
(58) Field of Classification Search ................. 536/23.1, 536/24.3, 26.6; 435/6.1
See application file for complete search history.

(56) References Cited

U.S. PATENT DOCUMENTS
5,808,300 A    9/1998  Caprioli
(Continued)

FOREIGN PATENT DOCUMENTS
DE    102 38 069 A1    3/2004
(Continued)

OTHER PUBLICATIONS

Office Action issued on Apr. 30, 2010, by the Examiner in U.S. Appl. No. 11/916,558.
(Continued)

*Primary Examiner* — Jezia Riley
(74) *Attorney, Agent, or Firm* — Foley & Lardner LLP

(57) ABSTRACT

The invention concerns a method for determining at least one target molecule map in a tissue section, using at least one (A-X)n-B conjugate, wherein A is a tag molecule of known molecular weight, X is a linker that is cleaved during sample desorption/ionization, n is an integer of at least 1, and B is a binding molecule that binds specifically to said target molecule. When using MALDI mass spectrometry, said linker molecule X may be cleaved by photodissociation during sample laser irradiation if photocleavable at the wavelength of said MALDI laser. Alternatively, when using UV-MALDI, IR-MALDI, SIMS or DESI mass spectrometry, said linker molecule X may be cleaved by fragmentation during sample desorption/ionization.

6 Claims, 10 Drawing Sheets

U.S. PATENT DOCUMENTS

| | | | |
|---|---|---|---|
| 6,635,452 | B1 | 10/2003 | Monforte et al. |
| 6,824,981 | B2 | 11/2004 | Chait et al. |
| 2002/0171037 | A1 | 11/2002 | Ellson et al. |
| 2005/0158863 | A1 | 7/2005 | Stahl et al. |
| 2006/0121535 | A1 | 6/2006 | Brueggemeier et al. |
| 2006/0198820 | A1 | 9/2006 | McDonald et al. |

FOREIGN PATENT DOCUMENTS

| | | |
|---|---|---|
| WO | WO 95/04160 A1 | 2/1995 |
| WO | WO 97/27327 A2 | 7/1997 |
| WO | WO 98/26095 A1 | 6/1998 |
| WO | WO 00/68434 A2 | 11/2000 |
| WO | WO 2004/051270 A2 | 6/2004 |
| WO | WO 2005/067648 A2 | 7/2005 |
| WO | WO 2005/113804 | 12/2005 |

OTHER PUBLICATIONS

Office Action issued on Sep. 11, 2009, by the Examiner in U.S. Appl. No. 11/916,558.

Moench, "In situ huybridization," *Molecular and Cellular Probes*, vol. 1, pp. 195-205, 1987.

Stoeckli et al., "Automated Mass Spectrometry Imaging with a Matrix-Assisted Laser Sesorption Ionization Time-of-Flight Instrument," *J. Am. Soc. Mass Spectrom.*, vol. 10, pp. 67-71, 1999.

U.S. Appl. No. 11/916,558, filed Dec. 5, 2007, Lemaire et al.

International Search Report mailed on Dec. 1, 2006 for application No. PCT/IB2006/002311.

Armstrong et al., *Anal. Chem.*, 2001, 73(15): pp. 3679-3686.

Sze et al., *J. Am. Soc. for Mass Spectrometry*, Feb. 1998, 9(2): pp. 166-174.

Mank et al., *Anal. Chem.*, 2004, 76(10), pp. 2938-2950.

Lemaire et al., *Anal. Chem.*, 2006, 78(3): pp. 809-819.

Caprioli et al., *Anal. Chem.*, 1997, 69(23): pp. 4751-4760.

Carda-Broch et al., *Rapid Commun. Mass Spectrom.*, 2003, 17: pp. 553-560.

Chaurand et al., *Proc. 52nd ASMS Conf. on Mass Spectrom. and Allied Topics*, May 23-27, 2004, Nashville, Tennessee.

Li et al., *J. Am. Soc. for Mass Spectrom.*, 2004, 15: pp. 1833-1837.

Zabet-Moghaddam et al., *Rapid Commun. Mass Spectrom.*, 2004, 18: pp. 141-148.

Stoeckli et al., *Nature Medicine*, Apr. 2001, vol. 7, No. 4, pp. 493-496.

Schwartz et al., *Journal of Mass Spectrometry*, 2003, vol. 38, pp. 699-708.

International Search Report issued on Oct. 8, 2007 in application No. PCT/IB2006/002309.

Caprioli et al., "Molecular Imaging of Biological Samples: Localization of Peptides and Proteins Using MALDI-TOG MS," *Anal. Chem.*, 1997, vol. 69, pp. 4751-4760.

Chaurand et al., "Profiling and Imaging Proteins in Tissue Sections by MS," *Analytical Chemistry*, American Chemical Society, Mar. 1, 2004, pp. 87A-93A.

Cooks et al., "Ambient Mass Spectrometry," *Science*, Mar. 17, 2006, vol. 311, pp. 1566-1570.

Karas et al., "Laser Desorption Ionization of Proteins with Molecular Masses Exceeding 10,000 Daltons," *Anal. Chem.*, American Chemical Society, 1988, vol. 60, pp. 2299-2301.

Touboul et al., "Improvement of Biological Time-of-Flight-Secondary Ion Mass Spectrometry Imaging with a Bismuth Cluster Ion Source," *J. Am. Soc. Mass. Spectrom.*, 2005, vol. 16, pp. 1608-1618.

Bai et al., "Design and synthesis of a photocleavable biotinylated nucleotide for DNA analysis by mass spectrometry," *Nucleic Acids Research*, 2004, vol. 32, No. 2, pp. 535-541.

Bai et al., "Photocleavage of a 2-nitrobenzyl linker bridging a fluorophore to the 5' end of DNA," *PNAS*, Jan. 21, 2003, vol. 100, No. 2, pp. 409-413.

Olejnik et al., "Photocleavable peptide-DNA conjugates: synthesis and applications to DNA analysis using MALDI-MS," *Nucleic Acids Research*, 1999, vol. 27, No. 23, pp. 4626-4631.

Levi-Setti et al., "Imaging of BrdU-Labeled Human Metaphase Chromosomes with a High Resolution Scanning Ion Microprobe," *Microscopy Research and Technique*, 1997, vol. 36, pp. 301-312.

Stoeckli et al., "Imaging mass spectrometry: A new technology for the analysis of protein expression in mammalian tissues," *Nature Medicine*, Apr. 2001, vol. 7, No. 4, pp. 493-496.

Walter, "Molecular Targeted Radiation Therapy," *S&TR*, Jul./Aug. 2003, pp. 10-11.

Wenzel et al., "Genosnip: SNP Genotyping by MALDI-TOF MS Using Photocleavable Oligonucleotides," *Nucleosides, Nucleotides & Nucleic Acids*, 2003, vol. 22, Nos. 5-8, pp. 1579-1581.

MBS

USE OF CONJUGATES WITH LINKERS CLEAVABLE BY PHOTODISSOCIATION OR FRAGMENTATION FOR MASS SPECTROMETRY ANALYSIS OF TISSUE SECTIONS

CROSS-REFERENCE TO RELATED APPLICATIONS

This application is a National Stage application of PCT/IB2006/002309, filed Jun. 7, 2006, which claims priority from US Provisional Application No. 60/687,848, filed Jun. 7, 2005.

SEQUENCE LISTING

The instant application contains a Sequence Listing which has been submitted in ASCII format via EFS-Web and is hereby incorporated by reference in its entirety. Said ASCII copy, created on Feb. 22, 2011, is named 65691537.txt and is 3,465bytes in size.

The invention concerns a method for determining at least one target molecule map in a tissue section, using at least one $(A-X)_n-B$ conjugate, wherein A is a tag molecule of known molecular weight, X is a linker that is cleaved during sample desorption/ionization, n is an integer of at least 1, and B is a binding molecule that binds specifically to said target molecule. When using MALDI mass spectrometry, said linker molecule X may be cleaved by photodissociation during sample laser irradiation if photocleavable at the wavelength of said MALDI laser. Alternatively, when using UV-MALDI, IR-MALDI, SIMS or DESI mass spectrometry, said linker molecule X may be cleaved by fragmentation during sample desorption/ionization.

Recently, transcriptome and proteome studies have led to the identification of many proteins implicated in a wide diversity of diseases, such as several kinds of cancers.

However, most of these results have been obtained on purified extracted nucleic acid or protein samples, which do not generate information on the tissue localisation of the incriminated proteins, although this kind of information is crucial for the understanding of physiological processes. Another shortcoming of most of the available data is that few studies have simultaneously analyzed the mRNA and protein expression of molecules of interest, which is nevertheless important to clarify the expression pattern of a particular protein. It would thus be very useful to have combined data of both mRNA and protein expression maps.

Current technologies for the tissue expression mapping of mRNA usually resort to nucleic acid probes coupled to radioactive, fluorescent or chemoluminescent markers after in situ hybridization (ISH). For protein expression mapping in tissue sections, usual technologies include immunohistochemistry and immunofluorescence.

The main drawback of all these technologies of tissue section expression mapping is that the number of target molecules that can be analyzed simultaneously is limited, even with fluorescent probes or antibodies, since no more than 3 or 4 distinct target molecules can be studied in the same experiment.

Mass spectrometry, on the other hand, allows for the simultaneous multiplex analysis of complex mixtures of biomolecules, depending on their molecular weight. In particular, Matrix Assisted Laser Desorption/Ionization (MALDI) mass spectrometry has become a powerful tool in the field of biological researches and is used for the detection, identification and characterization of nucleic acids, peptides and proteins from complex mixtures.

In particular, Olejnik and collaborators describe the synthesis and characterization of photocleavable peptide-DNA conjugates along with their use as photocleavable mass marker (PCMM) hybridization probes for the detection of immobilized synthetic target DNAs by matrix-assisted laser desorption/ionization (MALDI) mass spectrometry (Olejnik et al. Nucleic Acids Res. 1999 Dec. 1; 27(23):4626-31).

Patent application WO 98/26095 describes the synthesis and use of mass-labeled compounds to specifically interact with biomolecular targets. Patent application WO 00/68434 describes a method of detecting multiple analytes in a sample in a single assay, based on encoding target molecules with signals followed by decoding of the encoded signal.

However, no document in the prior art describes a method for the MALDI mass spectrometry (MALDI-MS) analysis of nucleic acids comprised in tissue sections.

The inventors have set up a new method for the detection of biomolecules, in particular mRNA, in tissue sections by MALDI-MS, using conjugates composed of a moiety that binds specifically to the target molecule(s), a moiety of known molecular weight (the "tag" moiety), and a photocleavable linker that is directly cut by the MALDI laser during the ionization process (see FIG. 1). This new method allows for the easy and precise indirect mapping of mRNA in tissue sections, and the use of tag moieties of widely dispersed molecular weights makes it possible to analyze a high number of distinct biomolecules simultaneously.

In addition, when this new method is used to map tissue expression of mRNA, a common picture of mRNA and corresponding protein expression can be obtained in two consecutive tissue sections. Indeed, several publications have shown that MALDI-MS could become an efficient tool for direct analysis of peptides and proteins in tissue sections (Caprioli, R. M.; Farmer, T. B.; Gile, J. *Anal. Chem.* 1997, 69, 4751-4760; Stoeckli, M.; Farmer, T. B.; Caprioli, R. M. *Nat. Med.* 2001, 7, 493-496; Chaurand, P.; Schwartz,. S. A.; Caprioli, R. M. *Anal. Chem.* 2004, 87A-93A).

Finally, the inventors have found that such a method is also transposable to mass spectrometry in general provided that the photocleavable linker is replaced by a linker which is cleaved by fragmentation during sample desorption/ionization. In this case, MALDI (UV-MALDI, or IR-MALDI), SIMS (Second Ion Mass spectrometry) or DESI (Desorption Electrospray Ionization) mass spectrometry may be used instead of MALDI, and preferably UV-MALDI, only. In addition, the inventors have found that conjugates with photocleavable linkers suitable for UV-MALDI analysis may also be used with other mass spectrometry technologies, since the chosen photocleavable linkers are also cleaved by fragmentation during sample desorption/ionization. The particular conjugates set up by the inventors may thus be used with any mass spectrometry technology suitable for tissue section analysis, notably with MALDI (UV-MALDI, or IR-MALDI), SIMS (Second Ion Mass spectrometry) or DESI (Desorption Electrospray Ionization) mass spectrometry.

The invention thus concerns a method for determining at least one target molecule map in a tissue section, comprising:
  a) hybridizing said tissue section with at least one $(A-X)_n$-B conjugate, wherein
    A is a tag molecule of known molecular weight,
    X is a linker that is cleaved during sample desorption/ionization,
    n is an integer of at least 1, B is a binding molecule that binds specifically to said target molecule, and each distinct B molecule is linked to a distinct A tag molecule;

b) scanning the tissue section surface and analyzing each adjacent spot with a mass spectrometer, wherein said linker X is cleaved during sample ionization, and wherein the resulting data of each spot is saved; and c) analyzing the obtained data in the molecular mass window(s) of each distinct tag molecule to create as many maps of the tissue section as the number of distinct studied target molecules.

According to the invention, a "tissue section" preferably has the following properties: it may be frozen or paraffin-embedded, its thickness is preferably in the order of a mammalian cell diameter, thus comprised between 5 and 20 μm. In the case of a frozen section that was obtained from a frozen tissue using a cryostat, OCT (optimal cutting temperature polymer) is preferably used only to fix the tissue but the frozen tissue is not embedded in OCT, so that tissue sections were not brought into contact with OCT. The tissue section may then be transferred on a MALDI plate composed of any material suitable for further MALDI analysis, including metals, inorganic or organic materials, such as gold, steel, glass fiber, glass, nylon 6/6, silicon, plastic, polyethylene, polypropylene, polyimide, polyvinylidenedifluoride or a glass slice of any thickness coated with conductive metal keeping transparency properties such as nickel or ITO.

According to the invention, a "target molecule" means a molecule of interest that is capable to specifically bind to another molecule, which is referred to as a "binding molecule". Such tandem target/binding molecules may display any chemical structure, providing that they are capable to generate a specific hybridization in a tissue section. A large variety of tandem target/binding molecules, as well as tandem binding/target molecules, are comprised in the scope of the present invention, including nucleic acids/nucleic acids, nucleic acids/peptides, nucleic acids/proteins, nucleic acids/antibodies, peptides/peptides, peptides/proteins, peptides/antibodies, proteins/proteins (in particular ligands/receptors), proteins/sugars, antigens/antibodies, haptens/antibodies, organic compounds/receptor (see some example in FIG. 2).

In particular, target nucleic acid sequences may be specifically detected using single stranded nucleic acid probes with a nucleic sequence that is complementary to the single-stranded target nucleic acid or to one of the strands of a double-stranded target nucleic acid (see FIG. 1). In the case of a target mRNA molecule, a nucleic acid probe complementary to the mRNA sequence may be used as binding molecule. Such a nucleic acid probe preferably has a nucleotide length comprised between 250 and 550, more preferably 300 to 500, 350 to 450, most preferably around 400.

Particular nucleic acid sequences may be detected using proteins or protein fragments (peptides) that specifically bind to the target sequence, such as for instance transcription factors or antibodies or antibody fragments that are specific for particular DNA sequences. For instance, auto-immune anti-DNA antibodies may be used.

In the case of peptides and proteins, all peptidic ligand/peptidic receptor tandem molecules that are known in the art are enclosed in the scope of the present invention. Such peptidic ligand/peptidic receptor tandem molecules includes peptidic antigens/antibodies or antibody fragments, as well as any hormone/hormone receptor, cytokine/cytokine receptor tandem, chemokine/chemokine receptor, aptamer/peptide, aptamer/protein. Membrane sugars that are implicated in cell migration and their proteic receptors are also in the scope of the present invention.

Also, antigens of any kind (such as nucleic acids, haptens, peptides or proteins) and their specific antibodies are included in the tandem target/binding and binding/target molecules according to the invention. In particular, the use of an antibody or antibody fragment as binding molecule in a conjugate allows for a novel kind of immunocytochemistry in tissue sections using MALDI-MS analysis as revelation technology thanks to the antibody photocleavably linked tag molecule.

Organic compounds may also be mapped using methods according to the invention. In particular, the in vivo distribution of administered organic drugs may be monitored using methods according to the invention.

In a particular embodiment of the above described method according to the invention, each target molecule is independently chosen in the group constituted of nucleic acids, in particular mRNA molecules, peptides, proteins, in particular receptors and ligands, antibodies, antigens, haptens, and organic compounds. In a preferred embodiment, at least one target molecule is a mRNA molecule. In another preferred embodiment, at least one target molecule is selected from a peptide, a protein, an antigen or a hapten.

In a particular embodiment of any above described method according to the invention, each binding B molecule that binds specifically to a target molecule is independently chosen in the group constituted of nucleic acids, particularly oligonucleotides, peptides, proteins, in particular receptors and ligands, antibodies, antigens, haptens, aptamers and organic compounds. In a preferred embodiment, when at least a target molecule is a mRNA molecule, each B molecule that binds specifically to a target nucleic acid is a nucleic acid probe with a sequence that is complementary to said target mRNA sequence. In another preferred embodiment, when at least a target molecule is a peptide, protein, antigen or hapten, each B molecule that binds specifically to a target peptide, protein, antigen or hapten is an antibody directed against said peptide, protein, antigen or hapten. In particular, when an antibody or antibody fragment is used as binding molecule B, the target molecule against which said antibody or fragment thereof is specifically directed may be the frame-work region of a particular antibody subclass, such as IgM, IgD, IgG, or IgE. Alternatively, when an antibody or antibody fragment is used as binding molecule B, the target molecule against which said antibody or fragment thereof is specifically directed may be the frame-work region of antibodies generated in a particular species, such as for instance rabbit, mouse, rat, goat, hamster, sheep and human. In these two cases, a 2 steps indirect detection may be performed using a primary non modified antibody of a specific subclass directed against any desirable target molecule, said primary antibody being then recognized by an antibody-tag conjugate according to the invention (see Example 2 and FIG. 3). Such a conjugate is highly advantageous since it permits to use it with any primary antibody, of any antigenic specificity, provided that said primary antibody belongs to the subclass recognized by the antibody of the conjugate.

According to the invention, a "tag molecule" refers to a molecule of known molecular weight that is detectable by mass spectrometry using MALDI (UV/IR), SIMS and DESI. A MALDI mass spectrometer usually allows for the detection of compounds in a wide range of m/z ratios. For instance, MALDI-Time of Flight (TOF) analyzers can detect compounds of m/z ratios up to 1 000 000. A suitable tag molecule also needs not to interfere with the specific binding of the target and the binding molecules. Preferably, a suitable tag molecule thus has limited steric volume to avoid steric hindrance of the binding of the target and binding molecules. For both above described reasons, suitable tag molecules thus preferably have a m/z ratio inferior to 10 000. Particular examples of suitable tag molecules include peptides, nucleic acids, sugars, polymers, lipids, and organic compounds. Among these, labelling molecules that are used to reveal a complex formation between a target molecule and a binding molecule, may also be used as tag molecules, including fluorochromes such as for instance usual fluorescein isothyocanate (FITC), R-phycoerythrin (PE), Cy3, Cy5, Cy7, PerCP, Allophycocyanin (APC), Texas Red, TRITC, PE-Cy5 conjugates, PE-Cy7 conjugates, or APC-Cy7 conjugates; enzymes such as alkaline phosphatase or peroxydase; biotin; gold; or all MALDI matrices or even all compounds that can be analyzed in pure laser desorption mode and for example pre-ionized molecules. When a mass spectrometry technology suitable for the detection of very small molecules is used, atoms may also be used as tag molecule.

All tag molecules described above may be used in the invention, and in any case, depending on the mass spectrometry technology used, a person even moderately skilled in the art of mass spectrometry analysis will know what type of tag molecule to choose to optimize the detection step. For instance, when MALDI mass spectrometry is used, tag molecules preferably have a m/z ratio<5000. Alternatively, when SIMS is used, tag molecules preferably have a m/z ratio<500, and when DESI is used, tag molecules preferably have a m/z ratio<5000.

In a particular embodiment of any above described method according to the invention, each A tag molecule is chosen in the group constituted of peptides, nucleic acids, sugars, and organic compounds. In a preferred embodiment, at least one A tag molecule is a peptide.

In a preferred embodiment of an above described method according to the invention, target molecule(s) are mRNA molecules, binding B molecule(s) are nucleic acid probes with a sequence complementary to mRNA sequences, and A tag molecule(s) are peptides. In a preferred embodiment of an above described method according to the invention, target molecule(s) are peptides, proteins (including antibodies), antigens, or haptens, binding molecules are antibodies or antibody fragments and tag molecules are peptides. In another preferred embodiment of an above described method according to the invention, target molecule(s) are peptides, proteins (including antibodies), antigens, or haptens, binding molecules are antibodies or antibody fragments and tag molecules are usual antibody labelling molecules such as fluorochromes, including for instance usual fluorescein isothyocanate (FITC), R-phycoerythrin (PE), Cy3, Cy5, Cy7, PerCP, allophycocyanin (APC), Texas Red, TRITC, PE-Cy5 conjugates, PE-Cy7 conjugates, or APC-Cy7 conjugates; enzymes such as alkaline phosphatase or peroxydase; or biotin or gold; or all MALDI matrices or even all compounds that can be analyzed in pure laser desorption mode and for example pre-ionized molecules.

According to the invention, "hybridizing said tissue section with at least one $(A-X)_n$-B conjugate" refers to a reaction in which the tissue section and the conjugate(s) are brought into contact in such conditions that the binding B molecule of the conjugate is able to bind specifically to its target molecule in the tissue section. Depending on the nature of the binding and the target molecule, well-known hybridization protocols are available to the ones skilled in the art. Indeed, in the case when the binding molecule is a nucleic acid probe, in situ hybridization in tissue section has been well documented and is thus easily available to a man skilled in the art. Antibody staining in tissue sections is also a routine technology which is easily available to a man skilled in the art.

Using a method according to the invention, it is thus possible to obtain a map of at least one target molecule in a tissue section. By a target molecule "map" in a tissue section is meant a two dimensional representation of the expression of said target molecule in said tissue section. This two dimensional representation is obtained by scanning the tissue section surface with the MALDI analyzer at a defined spot density, performing MALDI analysis on each successive spot and storing both the obtained data and the coordinates of each spot. The higher the spot density, the more precise is the resulting map. The diameter of a MALDI laser is generally between 50-200 µm depending on the focalisation of the system, so that two adjacent irradiation spots are preferably separated of the laser beam diameter (i.e. 50-200 µm). To allow for the acquisition of precise target molecule map, adjacent spots are preferably separated of at most 300 µm, at most 200 µm, more preferably at most 100 µm, at most 80 µm, at most 60 µm, at most 50 µm, at most 40 µm, most preferably of the diameter of the MALDI laser.

Each spot data is then analyzed in the molecular window of the tag molecule and the signal intensity of the tag molecule is reported at the spot coordinates. Such image reconstruction may be performed automatically using any suitable image reconstruction software known in the art or commercially available. Examples of suitable softwares are the IDL (Interactive Data Language) software, which is commercialized by RSI (RSI Corporate Headquarters. 4990 Pearl East Circle. Boulder, Colo. 80301), flexImaging (Bruker Daltonics, Bremmen, DE), MIT (M. Stoeckli, Novartis, Bâle, Switzerland).

In a method according to the invention for determining at least one target molecule map in a tissue section, several distinct target molecules can be mapped simultaneously. Indeed, it is sufficient to use several conjugates with distinct tag A molecules, thus displaying distinct molecular weights, to allow for the detection of several distinct target molecules. Using tag molecules with widely dispersed molecular weights, it is thus possible using any above described method according to the invention to map simultaneously the expression of many distinct target molecules in the same tissue section. In particular embodiments, at least 2, at least 3, at least 5, at least 8, at least 10, at least 15, at least 20, at least 30, at least 40, at least 50, at least 75, or at least 100 distinct target molecules may be mapped simultaneously. In particular, in the case of mRNA target molecules, at least 2, at least 3, at least 5, at least 8, at least 10, at least 15, at least 20, at least 30, at least 40, at least 50, at least 75, or at least 100 distinct target mRNA molecules may be mapped simultaneously in the same tissue section.

In a particular embodiment of any above described method in which target molecule(s) are mRNA molecule(s), said method may further comprise a step d) consisting in analyzing the obtained data in the molecular mass windows of each mRNA molecule corresponding protein to create each corresponding protein expression map of the tissue section.

In a first preferred embodiment, MALDI mass spectrometry is used and the X linker molecule is photocleavable at the wavelength of a MALDI laser. The invention then concerns a method for determining at least one target molecule map in a tissue section, comprising:

a) hybridizing said tissue section with at least one (A-X)
n-B conjugate, wherein
   A is a tag molecule of known molecular weight,
   X is a linker that is photocleavable at the wavelength of a MALDI laser,
   n is an integer of at least 1,
   B is a binding molecule that binds specifically to said target molecule, and
   each distinct B molecule is linked to a distinct A tag molecule;
b) scanning the tissue section surface and analyzing each adjacent spot with a MALDI mass spectrometer, wherein the MALDI laser is used both to release the tag molecule A and to induce the sample ionization, and wherein the resulting data of each spot is saved; and
c) analyzing the obtained data in the molecular mass window(s) of each distinct tag molecule to create as many maps of the tissue section as the number of distinct studied target molecules.

According to the invention, a "linker that is photocleavable at the wavelength of a MALDI laser" refers to a chemical compound that separates two other chemical moieties, and that may be cleaved at least at one site under exposition to a MALDI laser. Most MALDI lasers usually have an ultraviolet (UV: inferior to 500 nm) wavelength, usually between 300 and 500 nm. For instance, many UV-MALDI analyzers have a pulsed nitrogen laser with a wavelength of 337 nm. Thus, a linker according to the invention is, in a particular embodiment, efficiently cleaved at least at one site under exposition to a wavelength of 250 to 500 nm, preferably a wavelength of 320 to 360 nm or 320 to 350 nm, more preferably a wavelength of 337 nm, so that the UV-MALDI laser acts both to cleave the linker and to ionize the sample. Other MALDI analyser display an infrared (IR: superior to 770 nm) laser. For instance, a Nd:YAG laser (wavelength=1060 nm), Er:YAG laser (wavelength=2940 nm), a mid-infrared optical parametric oscillator (OPO) (wavelength=2940 nm) or a TEA-CO$_2$ laser (wavelength=10600 nm) may be used as IR-MALDI lasers. In other particular embodiments, a linker according to the invention is thus efficiently cleaved at least one site under exposition to a wavelength of 1000 to 1100 nm, preferably a wavelength of 1060 nm, or a wavelength of 2900 to 3000 nm, preferably a wavelength of 2940 nm, or a wavelength of 10500 to 10700 nm, preferably a wavelength of 10600 nm, so that respectively a Nd:YAG, a Er:YAG, or a TEA-CO$_2$ IR-MALDI laser acts both to cleave the linker and to ionize the sample.

In the case of UV-MALDI lasers, several linkers have been described (Olejnik et al. Nucleic Acids Res. 1999 Dec. 1; 27(23):4626-31; Bai X, et al. Nucleic Acids Res. 2004 Jan. 26; 32(2):535-41; Wenzel T et al. Nucleosides Nucleotides Nucleic Acids. 2003 May-August; 22(5-8):1579-81), and several reagents useful to introduce photocleavable linkers in organic molecules are commercially available, notably for instance from AmberGen™ (1106 Commonwealth Avenue. Boston, Mass. 02215, USA), Link Technologies (3 Mallard Way, Strathcycle Business Park, Bellshill, Lanarkshire ML4 3BF, Scotland), Integrated DNA Technologies (1710 Commercial Park ° Coralville, Iowa 52241, USA), Glen Research (22825 Davis Drive, Sterling, Va., 20164, USA), Eurogentec (EUROGENTEC s.a. Headquarters. LIEGE Science Park. Rue Bois Saint Jean 5. 4102 SERAING. BELGIUM).

In a particular embodiment of any above described method according to the invention in which MALDI mass spectrometry and a linker molecule X that is photocleavable at the wavelength of a MALDI laser are used, the X linker molecule comprises a moiety chosen in the group constituted of:

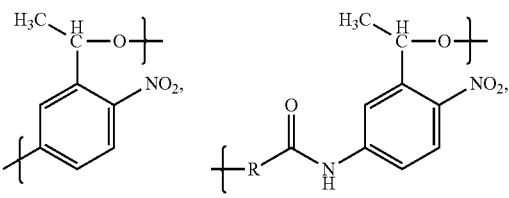

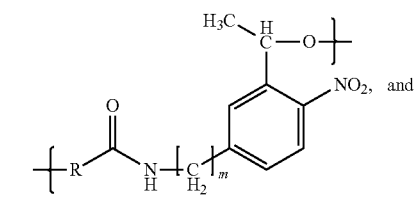

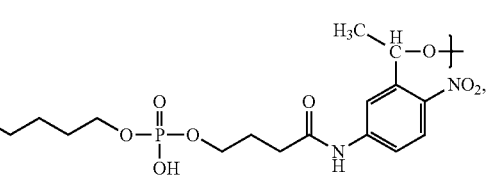

wherein R is a C1-C6 alkyl group and m is an integer comprised between 1 and 4.

Alternatively, said linker molecule X that is photocleavable at the wavelength of a MALDI laser are used, the X linker molecule comprises a moiety chosen in the group constituted of:

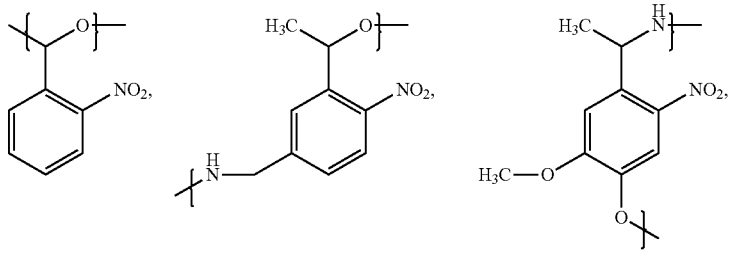

-continued

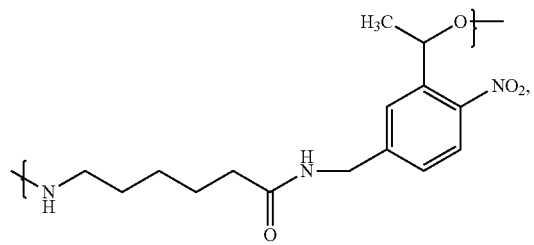

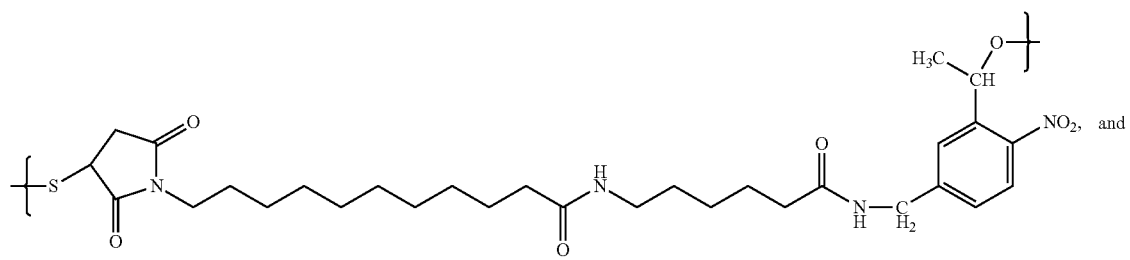

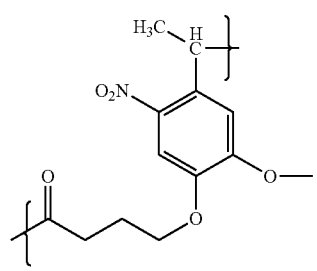

Linker molecules X linking a tag molecule A and a binding molecule B may be obtained between A and B using commercially available linkers comprising such moieties. For instance, linkers suitable for preparing conjugates with photocleavable linkers for use in a method according to the invention may be obtained from Glen Research Corporation (22825 Davis Drive, Sterling, Va. 20164, USA), including linkers named:

PC Linker (ref. 10-4920-02),
PC Spacer Phosphoramidite (ref. 10-4913-02), and
PC Amino Modifier (ref. 10-4906-02), or from Pierce (Pierce Biotechnology, Inc. Customer Service Department P.O. Box 117 Rockford, Ill. 61105 U.S.A), for instance linker Sulfo-KMUS (ref. #21111);

or from Merck Biosciences Ltd (Boulevard Industrial Park, Padge Road. Beeston, Nottingham NG9 2JR, United Kingdom) trade mark Novabiochem®, for instance linker

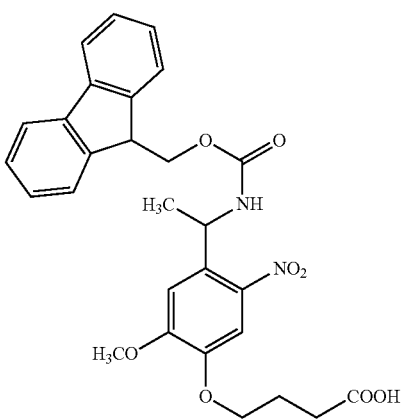

(ref. 01-60-0042);

or from Solulink under reference B1001, named Chromalink Biotin 354S, which is cleavable at a wavelength of 354 nm:

In a preferred embodiment where target molecule(s) are mRNA molecules, binding B molecule(s) are nucleic acid probes with a sequence complementary to mRNA sequences, and A tag molecule(s) are peptides, n is 1 is the (A-X)$_n$-B conjugate(s), and the resulting (A-X)-B conjugate(s) have the following structure:

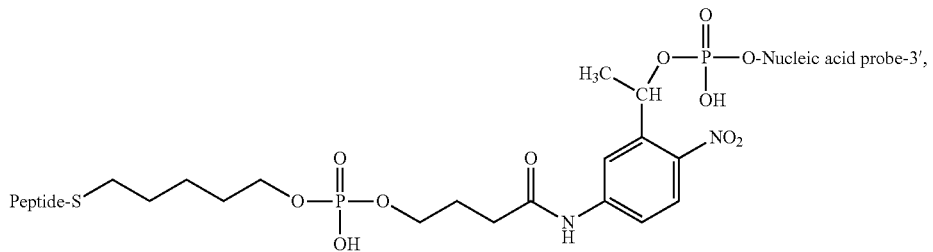

Such conjugates may for instance be obtained by amplification of a desired nucleic sequence using a forward (5') primer of the following structure:

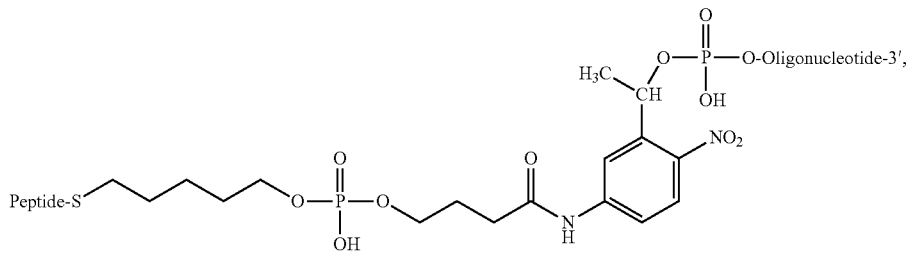

In another preferred embodiment where target molecule(s) are mRNA molecules, binding B molecule(s) are nucleic acid probes with a sequence complementary to mRNA sequences, and A tag molecule(s) are peptides, n is 1 is the (A-X)$_n$-B conjugate(s), and the resulting (A-X)-B conjugate(s) have the following structure:

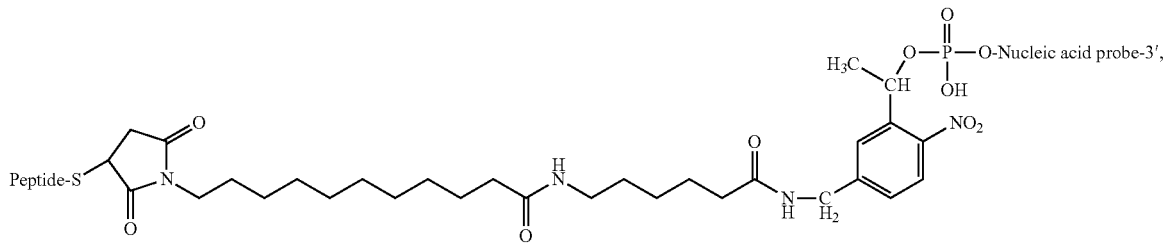

Such conjugates may for instance be obtained by amplification of a desired nucleic sequence using a forward (5') primer of the following structure:

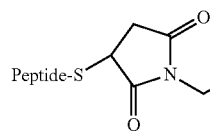 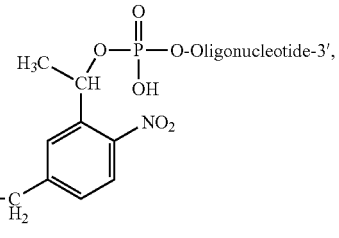

Alternatively, in another preferred embodiment where target molecule(s) are mRNA molecules, binding B molecule(s) are nucleic acid probes with a sequence complementary to mRNA sequences, and A tag molecule(s) are peptides, n is superior to 1 and the nucleic acid probe(s) comprise at least one modified base of the following structure:

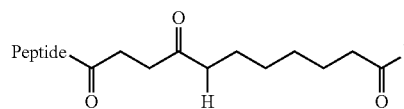 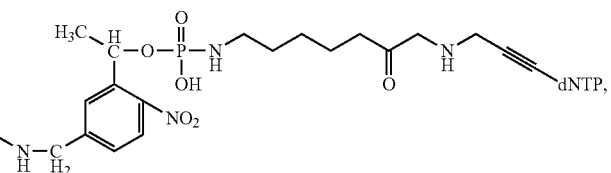

wherein "dNTP" means any triphosphate deoxynucleotide, including dATP, dCTP, dGTP, dTTP, and dUTP. In a preferred embodiment, a modified dUTP base is used.

In another preferred embodiment where target molecule(s) are mRNA molecules, binding B molecule(s) are nucleic acid probes with a sequence complementary to mRNA sequences, and A tag molecule(s) are peptides, n is superior to 1 and the nucleic acid probe(s) comprise at least one modified base of the following structure:

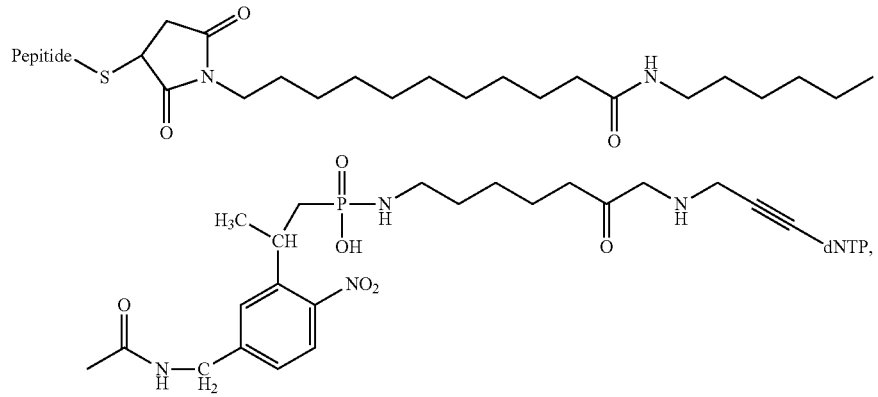

wherein "dNTP" means any triphosphate deoxynucleotide, including dATP, dCTP, dGTP, dTTP, and dUTP. In a preferred embodiment, a modified dUTP base is used.

With the use of such a modified peptide-tagged dUTP, peptide-tagged nucleic acid hybridization probes can be very simply generated using a simple PCR amplification in the presence of dATP, dCTP, dGTP and the modified peptide-tagged dUTP. This way, a specific hybridization probe can be easily synthesized for any target mRNA sequence.

Moreover, it allows for a signal amplification since a given hybridization probe synthesized with the modified peptide-tagged dUTP will carry as many tag peptides as the number of U bases in its sequence.

Finally, the use of hybridization probes synthesized with the modified peptide-tagged dUTP allows for a quantitative analysis of mRNA expression in tissue sections. Indeed, the signal generated by the corresponding tag(s) of one or several studied mRNA(s) can be compared with that obtained for a reference mRNA sequence (for instance a house-keeping gene such as actin of HPRT). As the number of U bases in each hybridization probe is known, the expression ratio between each studied mRNA sequence and the reference mRNA sequence can be calculated.

In a method where target molecule(s) are mRNA molecules, binding B molecule(s) are nucleic acid probes with a sequence complementary to mRNA sequences, and A tag molecule(s) are peptides, using conjugates described above, several distinct target mRNA molecules can be mapped simultaneously. Indeed, it is sufficient to use several conjugates with distinct nucleic acid probes and distinct tag peptides displaying distinct molecular weights, to allow for the detection of several distinct target molecules. Using tag peptides with widely dispersed molecular weights, it is thus possible using any above described conjugate to map simultaneously the expression of many distinct target mRNA molecules in the same tissue section. In particular embodiments, at least 2, at least 3, at least 5, at least 8, at least 10, at least 15, at least 20, at least 30, at least 40, at least 50, at least 75, or at least 100 distinct target mRNA molecules may be mapped simultaneously.

In addition, stored spectrum data also display direct peptide/protein analysis of the tissue section, so that the tissue section analysis method of target mRNA molecules using the conjugates described above may further comprise a last step d) consisting in analyzing the obtained data in the molecular mass windows of each mRNA molecule corresponding protein to create each corresponding protein expression map of the tissue section.

In a preferred embodiment where target molecule(s) are peptide(s), protein(s) (including antibodies) or hapten(s), binding B molecule(s) are antibodies directed against said target molecules, A tag molecule(s) are peptides, n is 1 and the (A-X)-B conjugate(s) have the following structure:

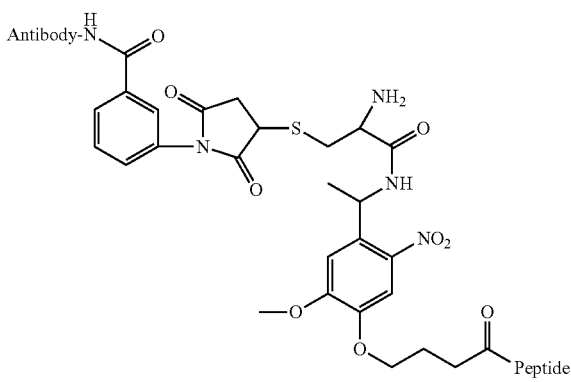

In any method according to the invention in which MALDI mass spectrometry is used, the matrix that is used for MALDI-MS analysis may be any classical MALDI matrix (e.g. CHCA, 2,5-DHB, SA, HABA, 3-HPA . . . ), or 2,4-DNPH.

By "matrix" is meant any material that, when mixed with the analyte, generates crystalline matrix-embedded analyte molecules that are successfully desorbed by laser irradiation and ionized from the solid phase crystals into the gaseous or vapour phase and accelerated as molecular ions. Commonly used MALDI-MS matrices are generally small, acidic chemicals absorbing at the laser wavelength, including nicotinic acid, cinnamic acid, 2,5-dihydroxybenzoic acid (2,5-DHB), α-cyano-4-hydroxycinnamic acid (CHCA), 3,5-dimethoxy-4-hydroxycinnamic acid (sinapinic acid or SA), 3-methoxy-4-hydroxycinnamic acid (ferulic acid), 3,4-dihydroxycinnamic acid (caffeic acid), 2-(4-hydroxyphenylazo)benzoic acid (HABA), 3-hydroxy picolinic acid (HPA), 2,4,6-trihydroxy acetophenone (THAP) and 2-amino-4-methyl-5-nitropyridine. Protocols for the preparation of these matrices are well-known in the art, and most of these matrices are commercially available. Current commonly used matrices for peptide/protein analysis include α-cyano-4-hydroxycinnamic acid (CHCA), 2,5-dihydroxybenzoic acid (2,5-DHB) and sinapinic acid (SA). DNPH is 2,4-Dinitrophenylhydrazine and is used for aldehydes and ketones detection.

In a second preferred embodiment of the invention, a linker molecule X that is cleaved by fragmentation during sample desorption/ionization is used, and the analysis is then not restricted to MALDI mass spectrometry, but generally transposable to any mass spectrometry technology suitable for tissue section analysis. In particular, UV-MALDI, IR-MALDI, SIMS or DESI mass spectrometry may be used.

Indeed, indirect detection of compounds necessitates a release of the tag molecule at the very beginning of the desorption and ion production in the source of the instrument. When using MALDI mass spectrometry, which uses a laser for ion desorption/ionization via energy absorption by the matrix molecules, several ways to induce the tag molecule release can be thought of. The first, most elegant, approach is to use photodissociation of the tag molecule by the MALDI laser irradiation (see FIG. 1 and FIG. 3). This means a very specific release but also necessarily more complex structures and synthesis.

However, fast fragmentation can also be considered as a way of releasing the tag molecule. This phenomenon is generally present in mass spectrometry technologies, and its use is thus compatible with MALDI and with other mass spectrometry sources. Notably, it can be taken advantage of this fragmentation phenomenon with other mass spectrometry technologies such as SIMS (Secondary Ion Mass Spectrometry), where the source is a primary ion beam, or with a recently described technology named DESI (Desorption Electrospray Ionisation). Moreover, as for MALDI/MS, these two technologies can be used for the direct analysis of tissue sections (Touboul, D.; Kolmer, F.; Niehis, E.; Brunelle, A.; Laprevote, O. Journal of the American Society for Mass Spectrometry, (JASMS) 2005, 15, 1608-1618) (Cooks, R. G. M.; Ouyang, Z. Takats, Z.; Wiseman, J. M.; Science, 17 Mar. 2006, Vol 311, 1566-1570).

Thus, the invention concept of using conjugates of a specific binding molecules linked to a tag molecule via a linker molecule can be transposed to other mass spectrometry technologies than MALDI, such as SIMS or DESI, provided that a linker that is cleaved by fast fragmentation is used, resulting in a fast fragmentation release of the tag molecule. Considering this phenomenon, it is possible to design other conjugates without more simple linkers, since they do not need to be photocleavable but only to be cleaved by fast fragmentation, which can be easily obtained. In fact, all sorts of linkers may be cleaved by fragmentation, and the capacity of any linker may be easily tested In addition, linkers that were described above as photocleavable at the wavelength of a MALDI laser were found by the inventor to be cleaved also by fast fragmentation. Alternatively, such linkers may thus be used in conjugates for any method according to the invention described above, including when other mass spectrometry technologies than MALDI are used, notably for SIMS or DESI mass spectrometry.

However, it must be clearly understood that the (A-X)n-B conjugates usable by taking advantage of the fast fragmentation phenomenon are not limited to the particular suitable linkers described above that may be cleaved by photodissociation and fragmentation. Indeed, the capacity to be cleaved by fast fragmentation of any linker that would permit an easy linkage between a A tag molecule and a B binding molecule is easily tested by simply analyzing the synthesized conjugate in solution and monitoring the presence of a cleaved A tag molecule. This way, any potential linker can be easily tested and approved or refused for use in the present invention. In addition, any person skilled in the art of mass spectrometry will know, for the great majority of potential linkers, if their chemical structure will or not permit there cleavage by fragmentation, so that the easy to perform test described above will even not be necessary in most cases.

In particular, conventional, and even commercial, labelled antibodies may be used as conjugates when fast fragmentation is used to cleave the linker. For instance, fluorescent conjugated antibodies may be used, the fluorescent molecule being used as tag molecule. Notably, FITC-conjugated, PE-conjugated, PerCP-conjugated, APC-conjugated, Cy3-conjugated, Cy5-conjugated, Cy7-conjugated, Texas red-conjugated, TRITC-conjugated, PE-Cy5-conjugated, PE-Cy7-conjugated, or APC-Cy7-conjugated antibodies may be used. Alternatively, antibodies conjugated to other molecules such as enzymes alkaline phosphatase or peroxydase may also be used, the enzyme being used as tag molecule. This possibility has the crucial advantage that all sorts of antibodies, with a very wide range of antigenic specificities, are commercially available as labelled antibodies. In addition, technologies to attach a labelling molecule via conventional linkers to any antibody are well-known routine technologies. This way, indirect mass spectrometry analysis of biomolecules present in tissue sections can be performed for a very large number of distinct biomolecules using the methods according to the invention.

Thus, in a preferred embodiment, when fast fragmentation is used, target molecule(s) are peptides, proteins (including antibodies), antigens, or haptens, binding molecules are antibodies or antibody fragments, n is 1 and tag molecules are fluorochromes, enzymes, biotin or gold. Atoms such as Br may also be conjugated to antibodies, in particular when SIMS mass spectrometry is used (see Example 4). In this case, a linker named EDAC commercially available from Sigma under reference E1769 may be used to conjugate the antibody to the Br atom (see Example 4).

In addition, when such a linker molecule X that is cleaved by fast fragmentation is used, potentially any mass spectrometry technology, provided that it is suitable for tissue sections analysis (which is immediately apparent for any skilled person), may be used to implement the method according to the invention. In particular, several additional mass spectrometry technologies than UV-MALDI or IR-MALDI may be used, such as SIMS or DESI mass spectrometry. Thus, in a preferred embodiment of a method in which a linker molecule X that is cleaved by fast fragmentation is used, UV-MALDI, IR-MALDI, SIMS or DESI mass spectrometry is used The invention further concerns a conjugate suitable for use in any method according to the invention, wherein said conjugate is selected from:

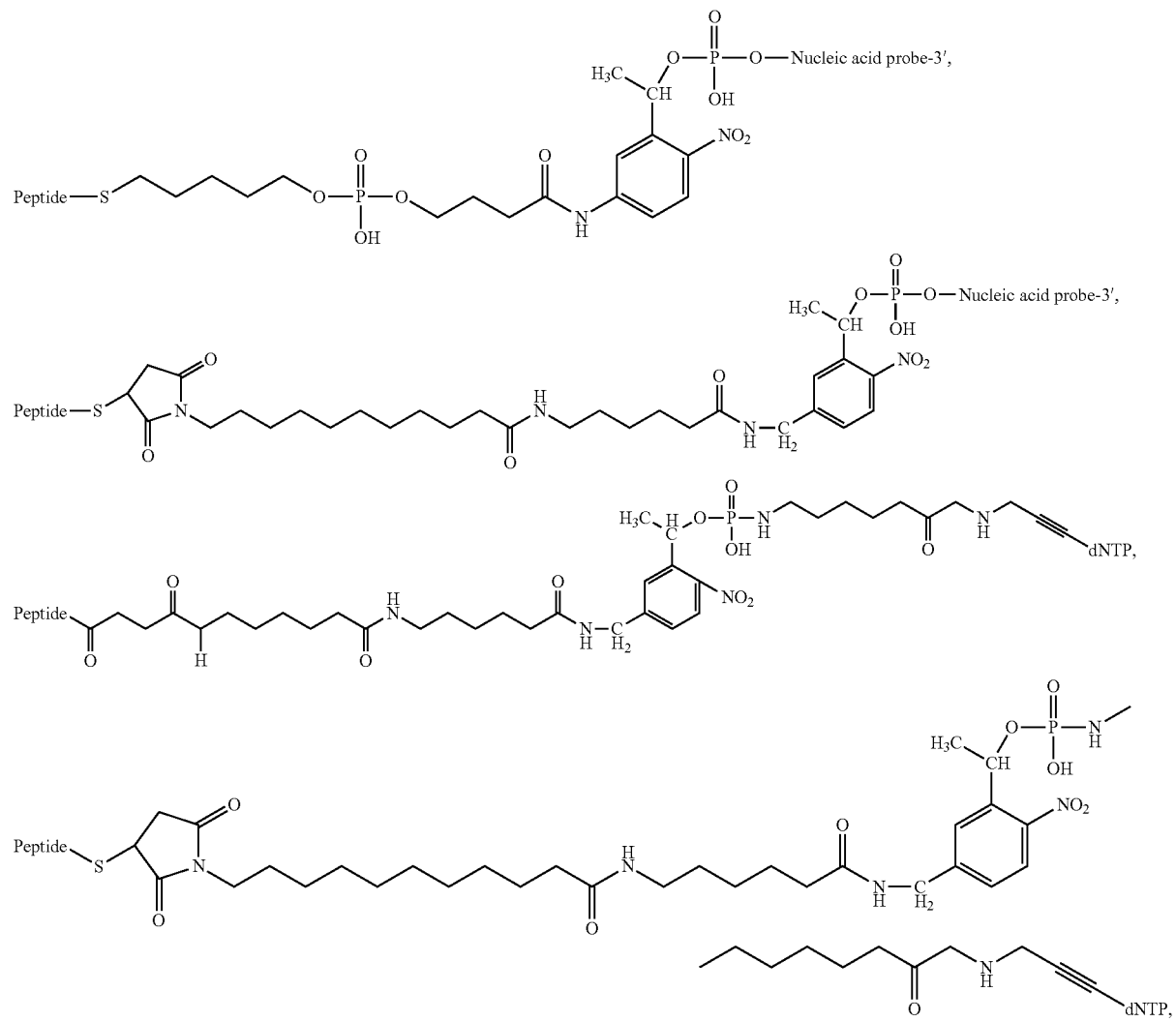

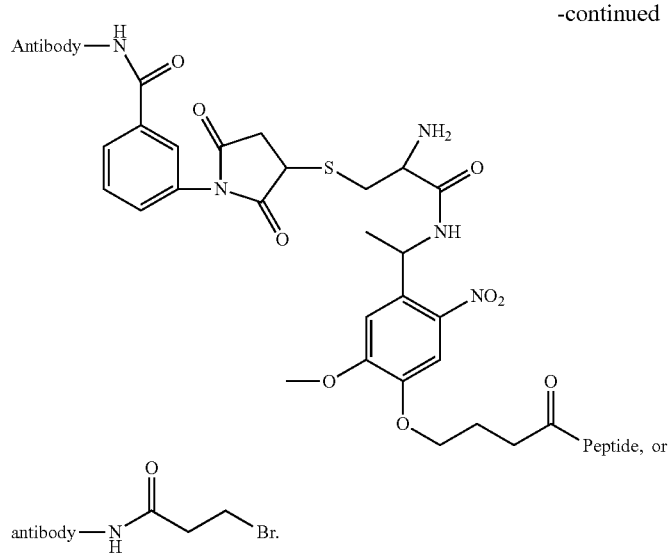

Each of the above conjugates is individually preferred as a conjugate according to the invention Having generally described this invention, a further understanding of characteristics and advantages of the invention can be obtained by reference to certain specific examples and figures which are provided herein for purposes of illustration only and are not intended to be limiting unless otherwise specified.

EXAMPLE 1

Figure 1:
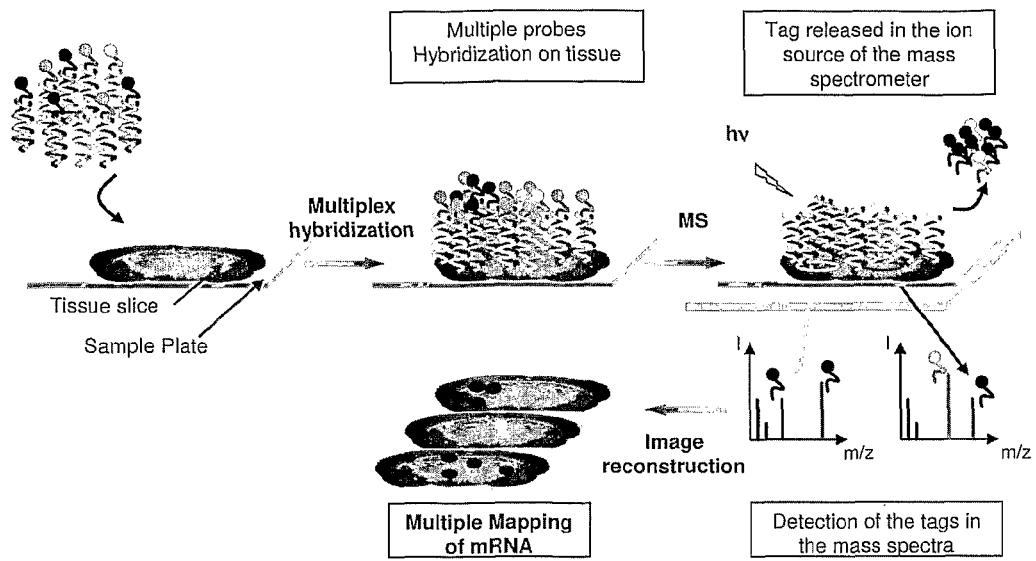
FIG. 1. Schematic principle of mRNA specific multiplex imaging by MALDI combining specifically designed labeled probes for indirect detection by tag molecule release during MALDI desorption/ionization step and ISH technology.
Figure 2:
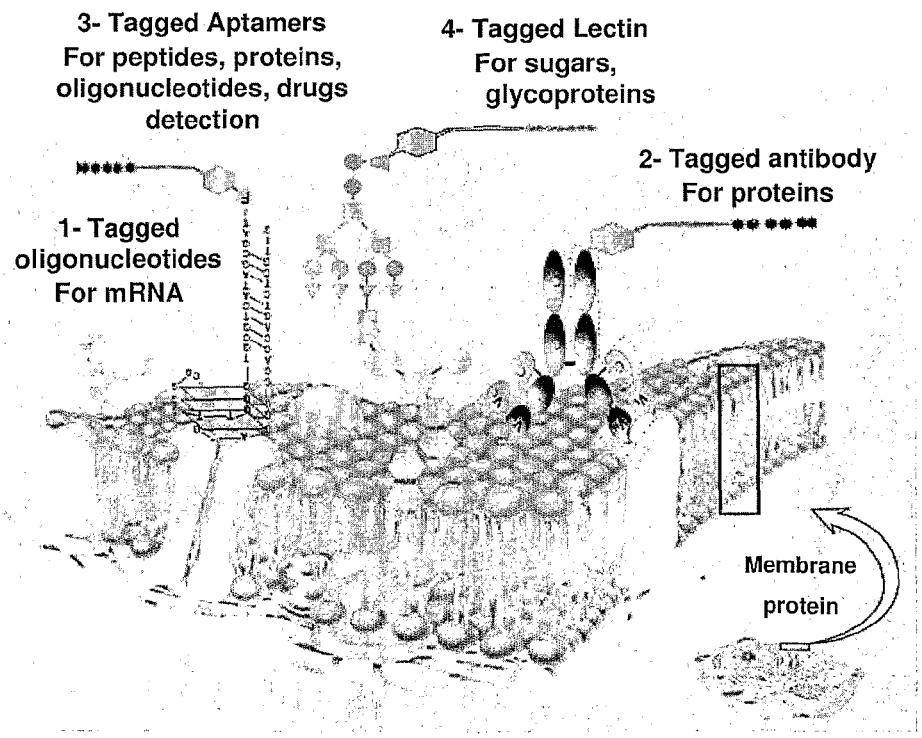
FIG. 2. General scheme of possible specific imaging of different targets (peptides, proteins, mRNA, sugars, drugs) using different labeled probes (oligonucleotides, antibodies, lectins, aptamers).
Figure 3:
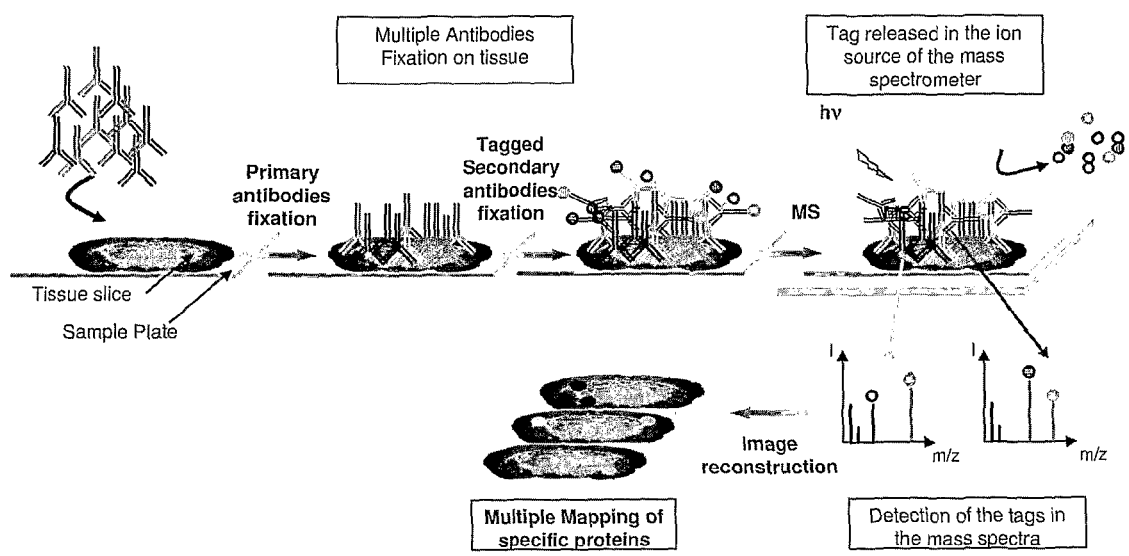
FIG. 3. Schematic principle of peptides/proteins multiplex specific imaging by MALDI combining specifically designed labeled probes for indirect detection by tag released during MALDI desorption/ionization step and immunocytochemistry technique.

Use of Oligo-Peptide Conjugates with a Photocleavable Linker for the Indirect Detection of mRNA is Tissue Sections by MALDI-MS Oligo-peptide conjugates with a photocleavable linker were tested for their capacity to allow indirect detection of specific mRNA in tissue sections by MALDI-MS.

1.1 Materials and Methods 1.1.1 Oligo-Peptide Conjugates

Structure

Oligo-peptide conjugates that were studied displayed the following structure:

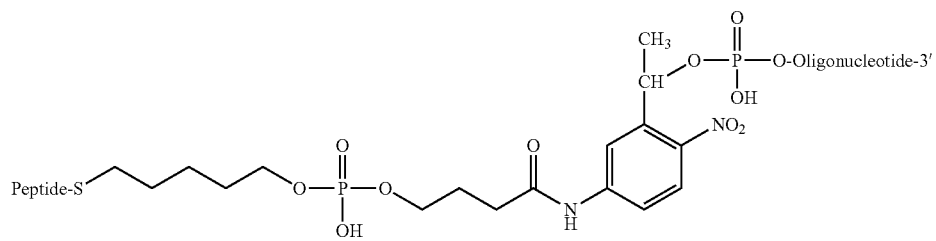

Five oligo-peptide conjugates with distinct peptide moieties were synthesized. The peptide amino acid sequence, monoisotopic ($M_{mono}$) and average ($M_{avg}$) molecular weights, and the nucleic sequence of the oligonucleotide of each conjugate are displayed in the following Table 2.

TABLE 2

Features of the studied oligo-peptide conjugates

| Oligo-peptide | Peptide sequence (N to C-terminal) | $M_{mono}$ (u.m.a) | $M_{avg}$ (u.m.a) | Oligonucleotide sequence (5'-3') |
|---|---|---|---|---|
| 1 | GRALGVFVC (SEQ ID NO: 1) | 918.50 | 919.14 | CACGTACAGGATGTACAG (SEQ ID NO: 6) |
| 2 | RPKPQQFFGLMC (SEQ ID NO: 2) | 1448.73 | 1449.79 | TCGAGAGGTACATCGTG (SEQ ID NO: 7) |
| 3 | RPPGFSPFRC (SEQ ID NO: 3) | 1160.58 | 1161.37 | AAGCGGTACGAGTAGCA (SEQ ID NO: 8) |
| Forward | RPPGFSPFRC (SEQ ID NO: 4) | 1718.00 | 1719.00 | GACGTACCAGGCGGTAGCTGCATTT (SEQ ID NO: 9) |
| Reverse | RPPGFSPFRC (SEQ ID NO: 5) | 1718.00 | 1719.00 | CAGGACTCCCCAAAGGAGAACAGGA (SEQ ID NO: 10) |

Synthesis

Oligo-peptide conjugates were synthesized using the following protocol:

The peptide is synthesized on Symphony (Protein Technologies Inc) and purified on a Delta-Pak C18 15 µm 100A column (Waters).

The oligonucleotide is synthesized from 3' to 5' on Expedite (ABI). The amine function with photocleavable linker is added in 5' before cleavage and deprotection. These steps are performed using a $NH_4OH$ 28% solution during 24 hours in the dark. The amino oligonucleotide is then purified on a Delta-Pak C18 15 µm 300A column (Waters). The amino function of the oligonucleotide is coupled to a heterobifunctional reagent comprising a maleimide function. The maleimido oligonucleotide is solubilized in water and added to an 1.2 equivalent of peptide in solution. The mixture is let under stirring for 16 hours.

The oligo-peptide conjugate is then purified on a Delta-Pak C18 15 µm 300A column (Waters) and characterized by mass spectrometry.

1.1.2 Preparation of Samples Before MALDI-MS

Several commonly used matrices were indifferently used for MALDI-MS analysis: α-cyano-4-hydroxycinnamic acid (CHCA), 3-hydroxy picolinic acid (HPA), and sinapinic acid (SA).

For CHCA, 10 mg of the matrix was dissolved in 1 mL of acetonitrile/water (2:1, v/v, 0.1% $TFA/H_2O$). For SA, 20 mg of matrix was dissolved in the same solvent.

For SA, 20 mg of matrix was dissolved in the same solvent.
For HPA, 50 mg/ml of the matrix was dissolved in water.

In some cases, an additive (ammonium citrate or acetate) was added to the matrix.

Before MALDI-MS analysis, 14 of sample solution and 14 of matrix solution were mixed on the MALDI plate according to the procedure of the dried-droplet preparation (Karas, M.; Hillenkamp, F.; *Anal. Chem.* 1998, 60, 2299-2301).

Three distinct MALDI plate materials have been tested: stainless steel, gold and Teflon.

1.1.3 MALDI-MS Analysis

MALDI-TOF mass spectra were performed on a Voyager-DE STR mass spectrometer (Applied Biosystems, Framingham, Mass., USA) with delayed extraction (DE) and operating with a pulsed nitrogen laser emitting at 337 nm.

Analysis in Linear Mode

For inox MALDI plates, acquisition parameters were set to: acceleration voltage: 20 kV; $1^{st}$ grid voltage: 94%; guide-wire voltage: 0.05%; extraction delay time: 100-250 ns.

For gold MALDI plates, acquisition parameters were set to: acceleration voltage: 25 kV; $1^{st}$ grid voltage: 96%; guide-wire voltage: 0.05%; extraction delay time: 600 ns.

Analysis in Reflector Mode:

Acceleration voltage: 20 kV, $1^{st}$ grid voltage: 70%, guide-wire voltage: 0.05%, extraction delay time: 200 ns.

1.1.4 Software for Image Reconstruction

For image reconstruction, software flexImaging (Bruker daltonics, Bremmen, DE) was used.

1.1.5 PCR Amplifications Using Oligo-Peptide Conjugates

PCR amplifications of proenkephalin were obtained using either tagged (peptide-photocleavable linker-oligonucleotide) or conventional (without the photocleavable linker and the peptide moiety) reverse (5'-CAG-GAC-TCC-CCA-AAG-GAG-AAC-AGG-A-3', SEQ ID NO:10, see Table 2) and forward (5'-GA-CGT-ACC-AGG-CGG -TAG-CTG-CAT-TT-3', SEQ ID NO:9, see Table 2) primers. Amplification products were then analyzed by electrophoresis in 2% agarose gel.

1.1.6 Synthesis of a dUTP-Peptide Conjugate with a Photocleavable Linker

A modified peptide-tagged dUTP with the following formula was synthesized:

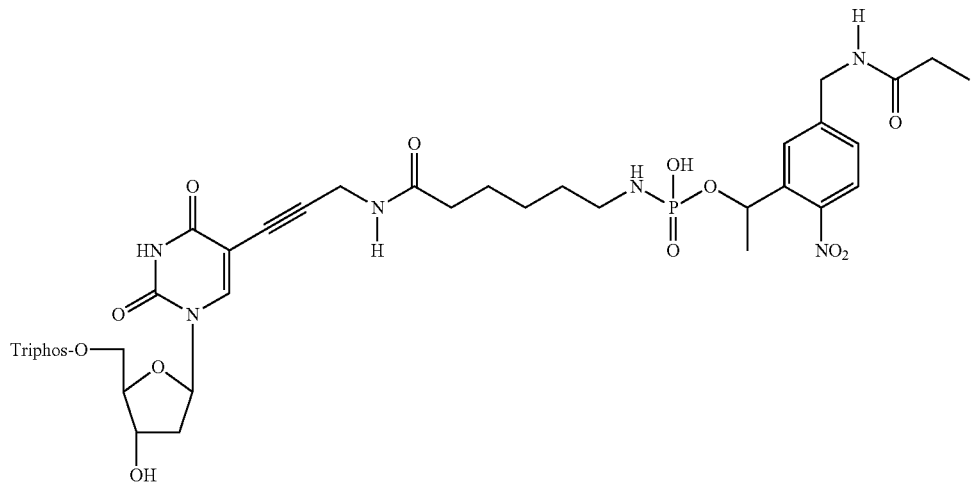

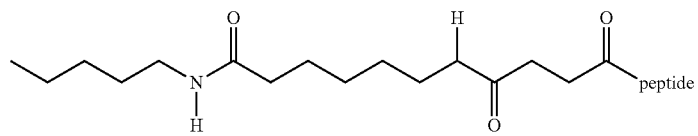

For the synthesis, the following synthesis scheme was followed:

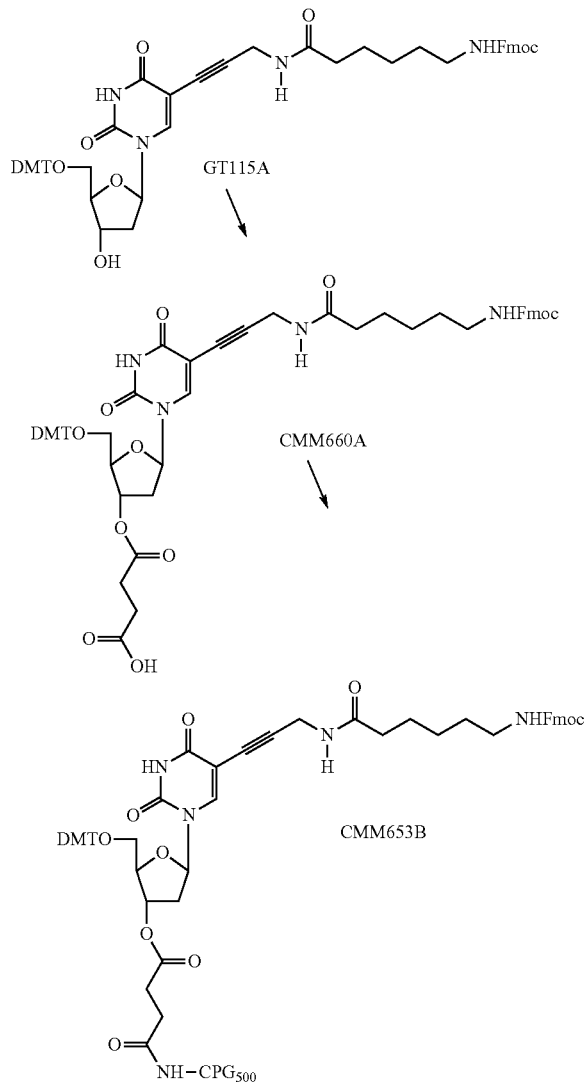

Scheme 1. Triphosphate from Fmoc-aminopropargylcaproyldU

In order to prepare this triphosphate a Fmoc protected CPG resin was required. Since none of the precursor was available, then the succinylate was prepared from GT115A (100 mg). The sample was relatively pure but contained a small amount (by TLC) of a higher running non-tritylated compound (originates from the Sonogashira reaction and does not interfere with subsequent reactions and was not visible in the nmr spectra of the sample). Since it was not possible to purify the succinate, the reaction was modified slightly. It is normal to add 2 equivalents of succinic anhydride to the reaction to get quantitative yield but if this is not removed completely the amino residues of the cpg resin can become blocked during functionalisation. Therefore, 1.5 equivalents were used since the exact purity of the product is undetermined. The reaction did not go to completion (from TLC this was more than 50% by comparing the intensity of the components on the TLC by UV (254 nm) and the intensity of the DMT cation on treatment with HCl fumes. Since the non-succinylated product will not react, the resin was functionalised using this mixture. The resin was prepared but the loading is very low, 5.4 $\mu molg^{-1}$ (180 mg).

The resin was detrytylated using 2% TCA/DCM washed with DCM and the process repeated until no orange colour due to the DMT cation was observed.

This was then dried (suction under argon) and the resin soaked in pyr/DMF 1:3 (0.4 ml) for 5 minutes before a solution of 0.1M Eckstein's reagent in dioxane was added (0.1 ml). The reaction was allowed to stand for 15 minutes after which time the resin was washed (dioxane, MeCN) and dried (suction under argon).

The resin was then soaked in a solution on 0.5M bis-(tributylammonium) pyrophosphate in anhydrous DMF and tri-n-butylamine for 20 minutes and the resin washed (DMF, MeCN) and dried (suction under argon).

The product was oxidised (iodine/water/pyridine/THF for 30 minutes), washed (MeCN) dried (suction under argon).

The Fmoc protecting group was removed (20% piperidine/DMF, 0.5 ml, 20 mins) and the resin washed thoroughly, (DMF, MeCN) and dried (suction under argon). This was then washed with DCI and a solution of DCI/photolabile amino linker CEP (1:1, 0.5 ml) was added and the reaction allowed to stand for 20 minutes. The solution was removed and the resin washed (MeCN) and dried (suction under argon). A mixture of cap A/cap B (1:1, 0.5 ml) was added and the resin soaked for 5 minutes before removing the capping reagents and washing and drying the resin as before. The product was oxidised ($I_2$/THF/pyr/$H_2O$, 5 mins) and the resin washed and dried as before. This was cleaved from the resin with cNH$_4$OH at room temperature for 30 mins, then purified by anion exchange HPLC on a Dionex NucleoPac100 HPLC column using the following solvent system Buffer A:0.1M NH$_4$Cl with 10% acetonitrile; Buffer B: 1M NH$_4$Cl with 10% acetonitrile; flow rate 2.5 mL/min. using 6-Triphos.mth. This gave 3 fractions (A:—7 mins, B:—7.9 mins and C:—10.3 mins). All 3 fractions were lyophilized over night before being desalted by reverse phase HPLC Buffer A: Water; Buffer B: acetonitrile; flow rate 4 mL/min. The 3 fractions were again lyophilized overnight before being suspended in 200 ul of water. M.S. showed that CMM661A pk 1 was definitely not the triphosphate but it could be either CMM661pk 2 or 3 (very similar M.S. profiles). (CMM662A was formed from CMM661A pk 2 and CMM663A was formed from CMM661A pk 3).

Both samples were then used in the subsequent reaction. Bicarbonate buffer (10 ul) and the maleimide NHS ester (50 ul) were added to each sample and the reactions agitated overnight. The samples were diluted with milliQ water (500 ul) and filtered. The samples were purified by RP-HPLC, buffer A: 0.1M TEAA, buffer B: MeCN, flow rate 4 mL/min. using MeCN50.mth and the coupling of the peptide was carried out on these fractions.

1.1.7 Synthesis of a Proenkephalin Nucleic Probe (400 bp) Incorporating the Modified, Peptide-Tagged dUTP A proenkephalin nucleic probe (400 bp) incorporating the previously synthesized modified, peptide-tagged dUTP (see paragraph 1.1.6) was synthesized by RT-PCR using the conventional forward and reward primers described in paragraph 1.1.5.

1.2 Results 1.2.1 Detection of One or Multiple Oligo-Peptide Conjugates in Various Modes of Analysis The three oligo-peptides conjugates were analyzed in various analysis modes, either separately or simultaneously (FIG. 4).

The analysis of separate oligo-peptide conjugates in linear positive mode (FIG. 4A), linear negative mode and reflector positive mode showed oligo-peptide conjugates are readily detectable in various MALDI analysis modes.

Sensitivity tests were also performed to assess the detection threshold in the various MALDI analysis modes. The observed thresholds were of 100 fmol with a signal/noise ratio of 8 in linear positive mode (FIG. 4B), and 1 pmol with a signal/noise ratio of 5 in reflector positive mode.

Figure 4A:
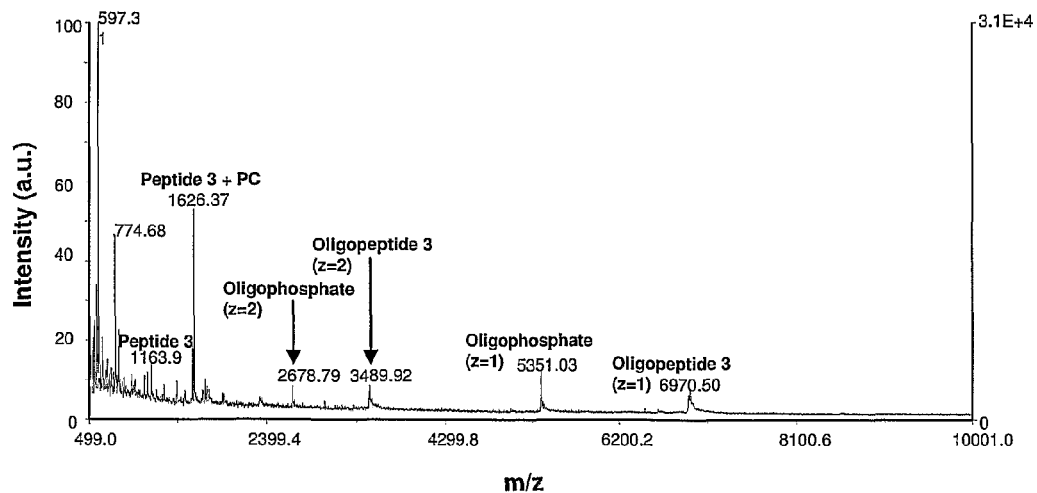
FIG. 4. Detection of the peptide moiety of A. oligo-peptide 3 in linear positive mode. B. 100 fmol of oligo-peptide 1 in linear positive mode C. oligo-peptides 1, 2 and 3 simultaneously in reflector positive mode, and D. oligo-peptide 3 on a MALDI support plate made of gold.
FIG. 4E shows the structure of an exemplary (A-X)-B conjugate.
Figure 4B:
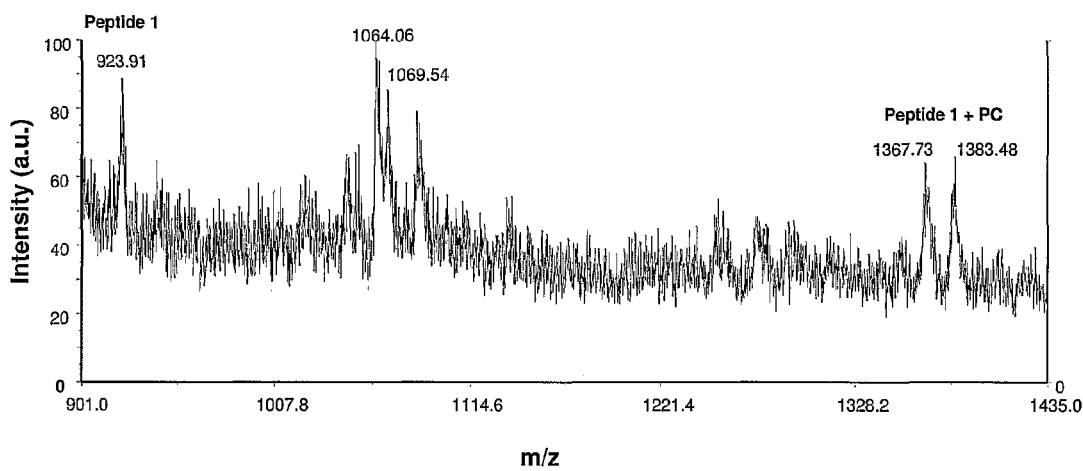
Figure 4C:
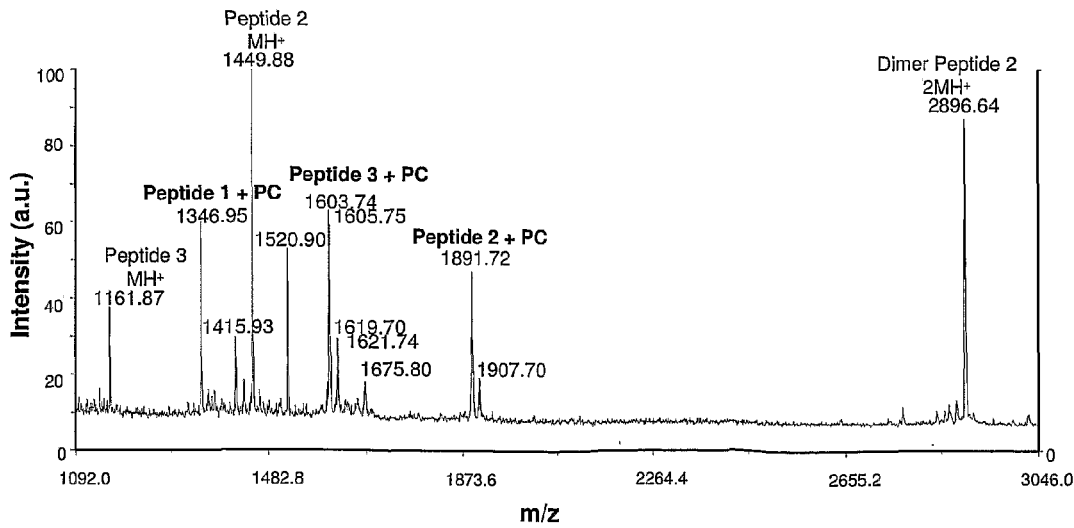

Oligo-peptides 1, 2 and 3 were further analyzed simultaneously in the linear positive mode, linear negative mode and reflector positive mode (FIG. 4C). In FIG. 4C, for each oligo-peptide conjugate, two peaks of distinct m/z ratios are observed. The higher m/z ratio peaks (m/z 1346.95, 1603.74 and 1891.72 respectively for peptides 1, 3 and 2) correspond to the photocleaved peptides at the expected cleavage site (containing the photocleavable linker). The lower m/z ratio peaks (m/z 1161.87 et 1449.88 respectively for peptides peptides 3 and 2) appear to correspond to a subsequent cleavage in gaseous phase leading to the formation of a protonated ion of peptide only (without the photocleavable linker).

In any case, these results show that three distinct oligo-peptides can be easily detected simultaneously.

The influence of the MALDI plate material on resolution, sensitivity and signal/noise ratio was investigated using stainless steel, gold and Teflon MALDI plates, with or without an additive composed of ammonium citrate or acetate.

Results show that cleavage of the photocleavable linker is possible no matter which material is used, with or without coating with ammonium citrate or acetate.

Figure 4D:
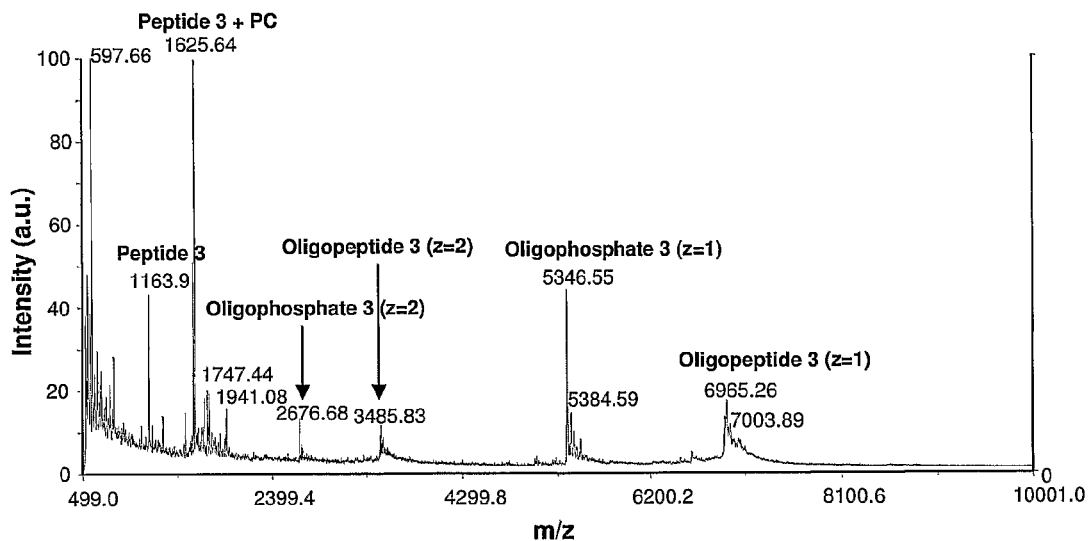
Figure 4E:
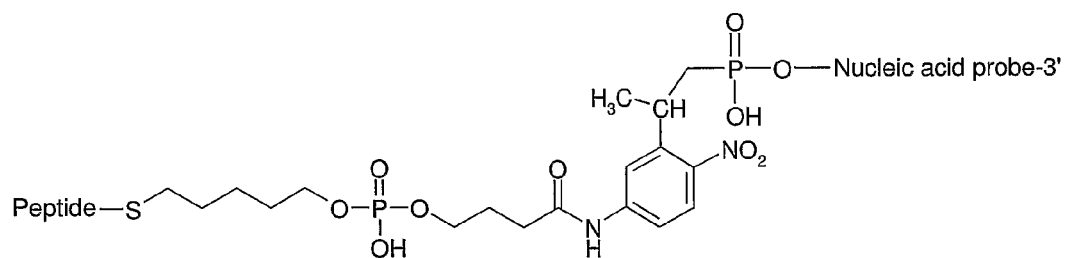

Moreover, it appears that the signal/noise ratio and signals intensity are higher on gold MALDI plates (FIG. 4D).

1.2.2 Mapping of an Oligo-Peptide Conjugate on a Solid Support

To evaluate the possibility to map an oligo-peptide conjugate on a surface, the image of an X letter made of oligo-peptide 3 was drawn using a multipipette on a MALDI plate.

The corresponding area was then analyzed, spot by spot, by MALDI-MS and the repartition of the ion m/z 1626.37 corresponding to the photocleaved fragment of oligo-peptide 3 under its sodium cationized form MNa$^+$ was reconstructed using image reconstruction software.

Figure 5:
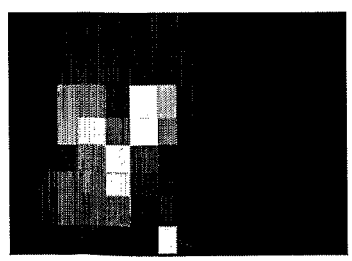
FIG. 5. Mapping of oligo-peptide 3 on a solid support. Oligo-peptide 3 was deposited with a multipipette on a solid support to draw the image of a X letter. The presence of oligo-peptide 3 was then mapped by MALDI-MS analysis and the image was reconstructed using IDL software. The resulting image is displayed FIG. 6. Synthesis of a peptide-tagged proenkephalin in situ hybridization probe A. PCR amplification products of proenkephalin obtained using either tagged (peptide- photocleavable linker-oligonucleotide) or conventional (without the photocleavable linker and the peptide moiety) forward (5'- CAG-GAC-TCC-CCA-AAG-GAG-AAC- AGG-A-3' (SEQ ID NO: 10)) and reward (5'-GA-CGT-ACC-AGG-CGG-TAG-CTG-CAT-TT-3' (SEQ ID NO: 9)) oligonucleotides. Line 1: conventional forward and reward primers. Line 2: tagged forward and conventional reward primers. Line 3: conventional forward and tagged reward primers. Line 4: tagged forward and tagged reward primers. Line 5: negative control: water control. Line 6: molecular weight markers. B. Corresponding amplification products after purification on silica columns. Line 1: conventional forward and reward primers. Line 2: tagged forward and conventional reward primers. Line 3: conventional forward and tagged reward primers. Line 4: tagged forward and tagged reward primers. Line 5: negative control: water control. Line 6: molecular weight markers. C. and D. MALDI analysis of purified PCR amplification products with tagged forward and reward primers (C.) or tagged forward and conventional reward primers (D.).

FIG. 5 shows the obtained reconstructed image, demonstrating the possibility to obtain a simple image from direct cleavage.

1.2.3 Synthesis of a Peptide-Tagged Proenkephalin In Situ Hybridization Probe Using Oligo-Peptide Conjugates as Primers To confirm the possibility to synthesize larger hybridization probes using an oligo-peptide conjugate as forward and/or reward primer, PCR amplifications were carried out using either tagged (peptide-photocleavable linker-oligonucleotide) or conventional (without the photocleavable linker and the peptide moiety) reverse (5'-CAG-GAC-TCC-CCA-AAG-GAG-AAC-AGG-A-3' (SEQ ID NO: 10)) and forward (5'-GA-CGT-ACC-AGG-CGG-TAG-CTG-CAT-TT-3' (SEQ ID NO: 9)) primers.

Figure 6:
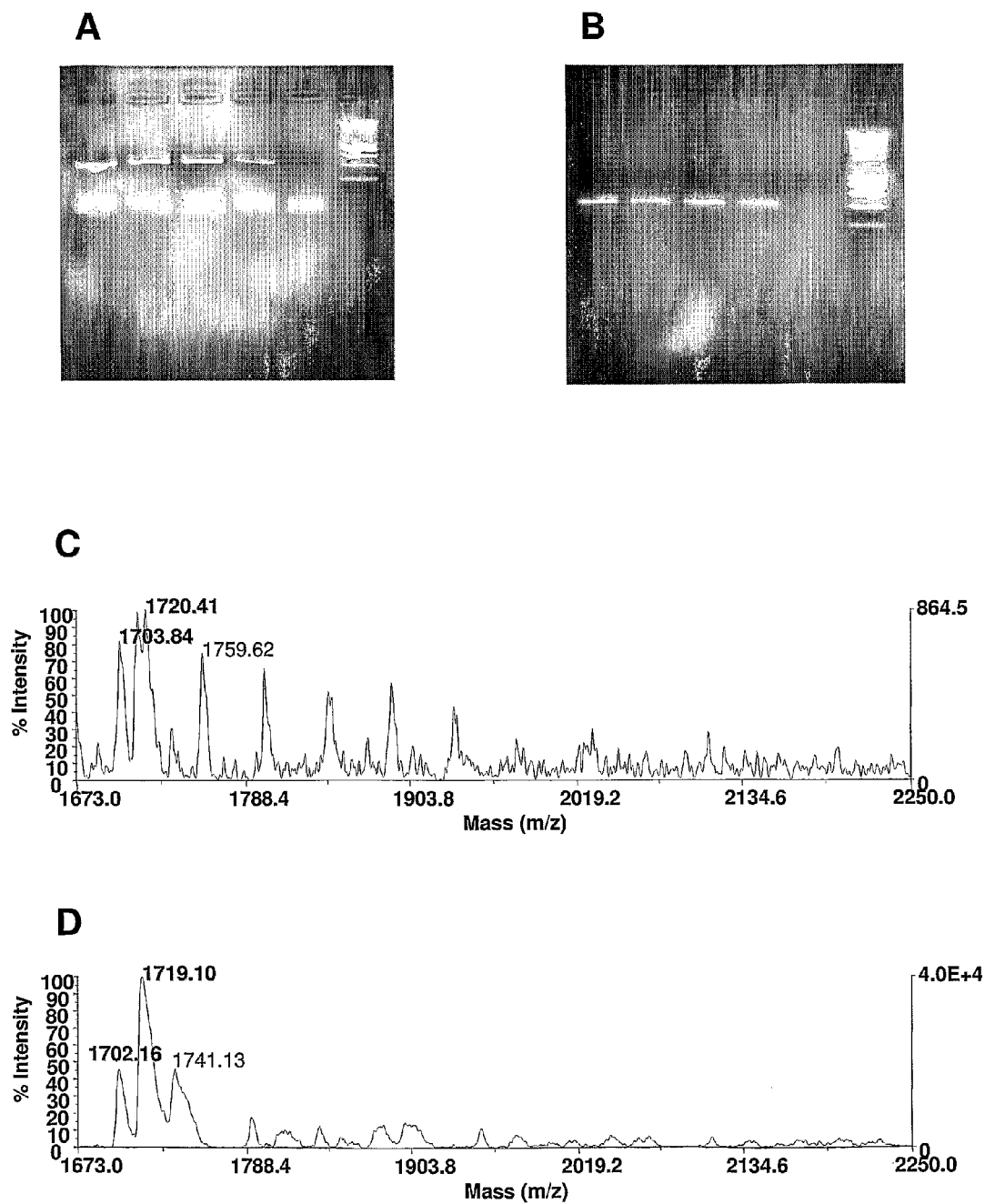

The resulting amplification products are displayed in FIG. 6A. The obtained results show that the use of forward and/or reward peptide-tagged primers does not inhibit the amplification and results in a proenkephlain in situ hybridization probe of around 400 bp.

After silica column purification, non amplified primer dimers were removed and pure PCR amplification products were obtained (FIG. 6B).

MALDI analysis of these purified PCR amplification products was carried out. Results obtained with both tagged forward and reverse primers (FIG. 6C) and with a tagged forward and a conventional reward primers (FIG. 6D) show that, despite the presence of significant amounts of PEG, the peptide tag is cleaved and can be detected. Indeed, although the m/z ratio of the cleaved peptide (m/z=1704) may be in some cases attributed to a PEG signal, the characteristic ion (M-NH$_2$)$^+$ with a m/z ratio of 1720 can be easily detected.

1.2.4 Proenkephalin mRNA Analysis in a Deparaffined Rat Brain Section Using a Peptide-Tagged Hybridization Probe In situ hybridization was performed on a deparaffined rat brain section using a peptide-tagged hybridization probe, as described before.

MALDI analysis was then performed on different tissue localizations and the resulting spectra analyzed.

Figure 7:
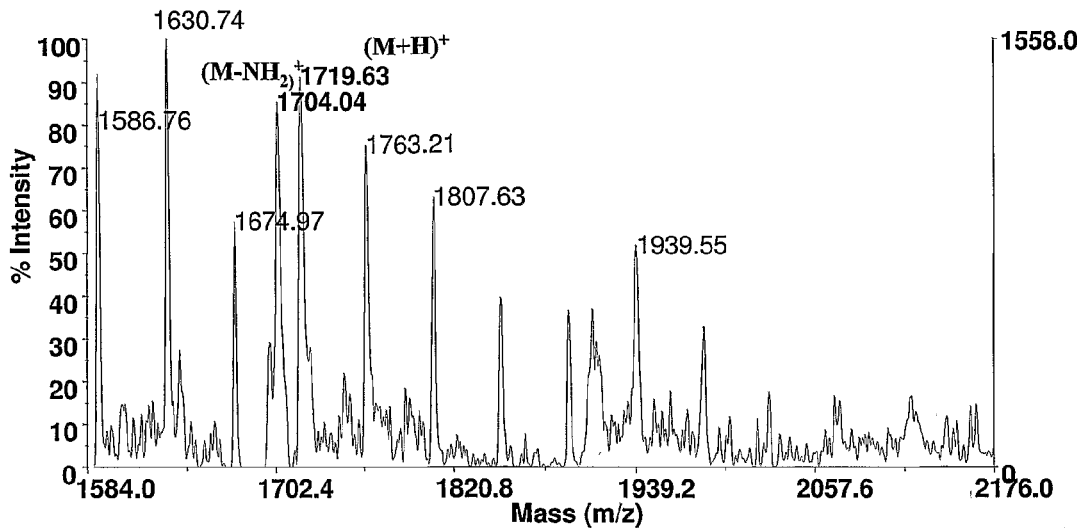
FIG. 7. Direct MALDI analysis of a deparaffined rat brain section after hybridization of a peptide-tagged proenkephalin in situ hybridization probe. A. First tissue section localisation. B. Second distinct tissue section localisation. C. Control analysis with a non peptide-tagged proenkephalin in situ hybridization probe.
Figure 7:
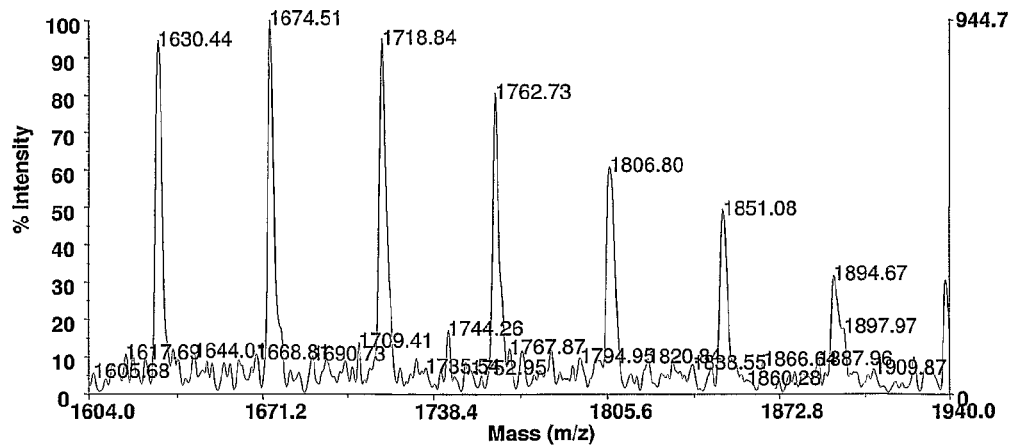
Figure 7:
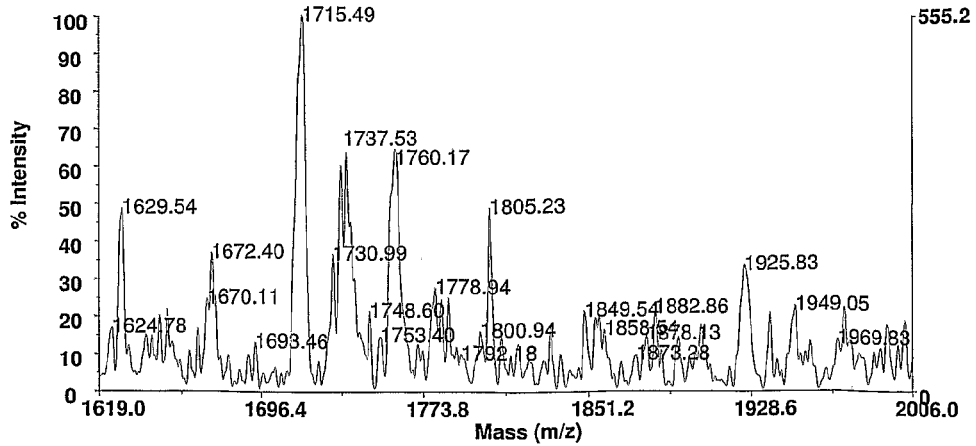

FIG. 7 shows the obtained spectra in two distinct brain section localizations (FIGS. 7A and B), as well as a control spectrum obtained by analysis of a control brain section which was hybridized with a non peptide-tagged hybridization probe.

The control spectrum shows that no signal is detected at the m/z ratios of the cleaved peptide (m/z=1704) or the characteristic ion (m/z=1720) when using a non peptide-tagged hybridization probe.

In contrast, proenkephalin mRNA expression can be clearly identified in the FIG. 7A brain section localisation (see peaks at m/z=1704 and 1720), while no proenkephalin mRNA expression can be detected at the second distinct localization (FIG. 7B, no peak at m/z=1704 or 1720).

The mRNA expression of proenkephalin can thus be clearly monitored at distinct spots of the tissue section, thus allowing to further reconstruct an image of the tissue section proenkephalin mRNA expression.

1.2.5 Synthesis of a dUTP-Peptide Conjugate with a Photocleavable Linker and Use of Such a Modified, Peptide-Tagged dUTP to Generate a Multi-Peptide-Tagged Proenkephalin Probe (400 bp).

With the synthesis protocol described in the Material and Methods section, a modified peptide-tagged dUTP nucleotide has thus been synthesized, with the formula displayed on FIG. 8A.

The modified peptide-tagged dUTP was analyzed by MALDI analysis to confirm the detection of the peptide tag. As shown on FIG. 8B, the peptide tag is clearly detected at the expected 1163.23 M+H$^+$.

With the use of such a modified peptide-tagged dUTP, a multi-peptide-tagged nucleic acid hybridization probe for proenkephalin has been very simply generated using a simple RT-PCR amplification in the presence of dATP, dCTP, dGTP and the modified peptide-tagged dUTP, as displayed on FIG. 8A This way, a specific hybridization probe could be easily synthesized for any other target mRNA sequence.

To confirm that the modified peptide-tagged dUTP was readily incorporated into the proenkephalin probe, the purified PCR product of proenkephalin amplified with either the modified peptide-tagged dUTP or a non modified dUTP with no tag was analyzed using MALDI analysis.

Figure 8:
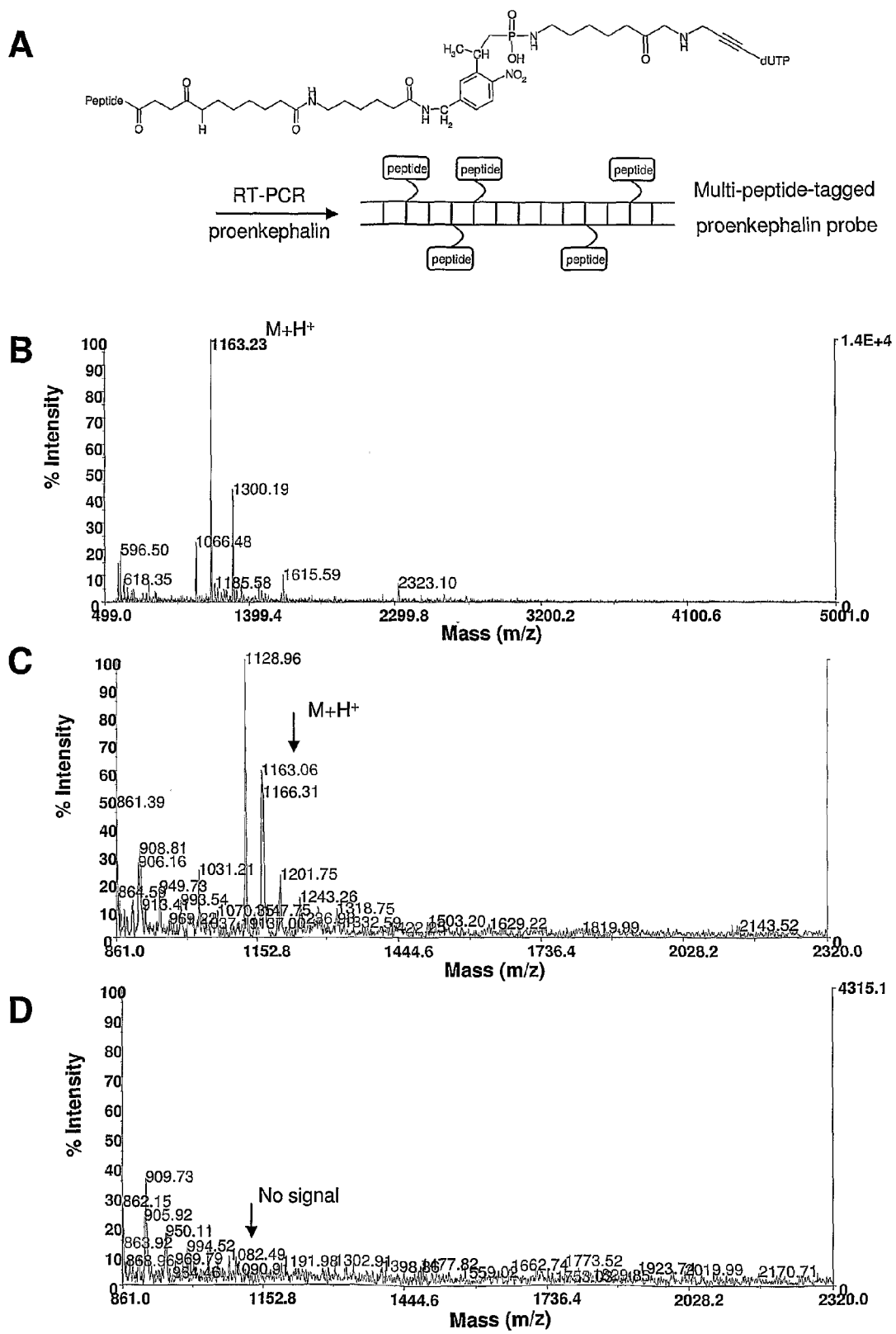
FIG. 8. Synthesis and MALDI analysis of a nucleic probe incorporating a modified, peptide-tagged dUTP. A. Structure of the modified, peptide-tagged dUTP and scheme of the RT-PCR synthesis of a proenkephalin nucleic probe (400 bp) incorporating the modified, peptide-tagged dUTP. B. MALDI analysis of the modified, peptide-tagged dUTP. C. MALDI analysis of the proenkephalin nucleic probe incorporating the modified, peptide-tagged dUTP. D. MALDI analysis of a proenkephalin nucleic probe incorporating a normal non modified dUTP, without peptide tag.

As shown on FIG. 8, the peptide tag is readily detected in the sample of proenkephalin amplified with the modified peptide-tagged dUTP at the expected 1163.06 M+H$^+$ (FIG. 8C), whereas no signal at the expected M+H$^+$ is detected in the sample of proenkephalin amplified with a non modified dUTP with no tag (FIG. 8D).

Moreover, the use of a modified, peptide-tagged dUTP allows for a signal amplification since a given hybridization probe synthesized with the modified peptide-tagged dUTP will carry as many tag peptides as the number of U bases in its sequence.

Finally, the use of hybridization probes synthesized with the modified peptide-tagged dUTP allows for a quantitative analysis of mRNA expression in tissue sections. Indeed, the signal generated by the corresponding tag(s) of one or several studied mRNA(s) can be compared with that obtained for a reference mRNA sequence (for instance a house-keeping gene such as actin of HPRT). As the number of U bases in each hybridization probe is known, the expression ratio between each studied mRNA sequence and the reference mRNA sequence can be calculated.

1.3 Conclusion

These results clearly demonstrate the possibility to use nucleic acid-photocleavable linker-peptide conjugates for the indirect simultaneous detection of multiple mRNA target molecules in tissue sections, using hybridization probes synthesized with peptide-tagged primers.

Moreover, a modified peptide-tagged dUTP has been synthesized that allows for an easier synthesis of peptide-tagged hybridization probes with any target mRNA specificity, an amplified tag signal, thus lowering the detection threshold, and the possibility to perform a quantitative mRNA expression analysis in tissue sections.

Thus, the indirect simultaneous mapping of several distinct mRNA target molecules in tissue sections using MALDI-MS analysis is now possible, with low detection threshold, possible multiplex analysis, and even possible quantitative analysis.

EXAMPLE 2

Use of an Antibody-Peptide Conjugate with a Photocleavable Linker for the Indirect Detection of a Protein is Tissue Sections by MALDI-MS An antibody-peptide conjugate with a photocleavable linker was synthesized and tested for its capacity to allow indirect detection of a specific protein in tissue sections using MALDI-MS.

2.1 Synthesis of the Antibody Peptide Conjugate

A goat antibody specific for the framework region of rabbit antibodies (goat anti-rabbit antibody) has been used to synthesize an antibody-peptide conjugate with a photocleavable linker at UV-MALDI laser wavelength. This way, the conjugate is suitable as secondary antibody for the indirect analysis of any peptide, protein, antigen or hapten for which a primary rabbit antibody is available. In addition, it has to be noted that the protocol of synthesis described below is applicable to any antibody of any specificity, including any peptide, protein, antigen or hapten, so that other conjugates in which the antibody is specific for another type of antibody or for any desirable peptide, protein, antigen or hapten may be easily synthesized using the protocol described below.

As tag molecule, a peptide was used displaying the following formula: DSPEGLNRKQKPA (SEQ ID NO: 11). However, in this case also, the protocol described below is applicable to any other peptide that might be desirable a tag molecule.

The peptide was synthesized in solid phase and directly coupled to the photocleavable linker, resulting in a peptide-phocleavable compound of formula (SEO ID NO: 11):

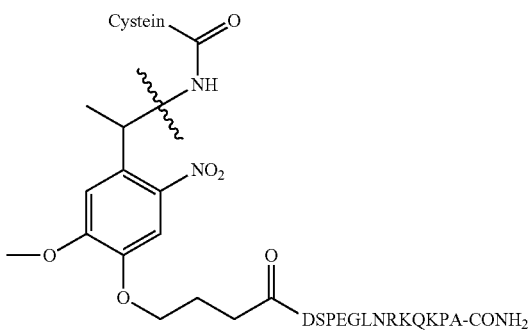

The antibody-peptide conjugate was synthesized using the following reaction steps:
1. solid phase peptide synthesis with photocleavable linker (classical Fmoc strategy)
2. Purification of peptide using RP-HPLC (C18) using water/acetonitrile+0.5% TFA
3. 0.5 mg of MBS dissolved in 300 µl of DMF
4. 4 mg IgG (goat anti rabbit) was dissolved in 2 ml of PBS
5. Mix slowly product 3 et 4. Reaction occurs under agitation during 30 min at 20° C.
6. salts were removed using PD10 with phosphate buffer 50 mM pH 6
7. 1 mg of peptide was dissolved in 300 µl of DMF then 1 ml de PBS was added.
8. Add this peptide solution on active antibody solution; the reaction occurs under agitation during 3 h at 20° C. in the dark.
9. PBS was removed by dialysis overnight.

Figure 9:
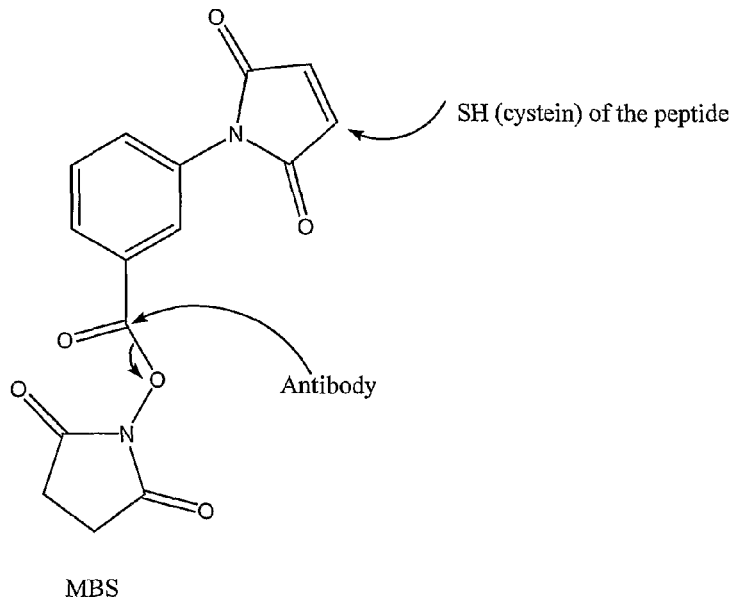
FIG. 9. Reactions for the synthesis of an antibody-peptide conjugate with a photocleavable linker X.
Figure 10:
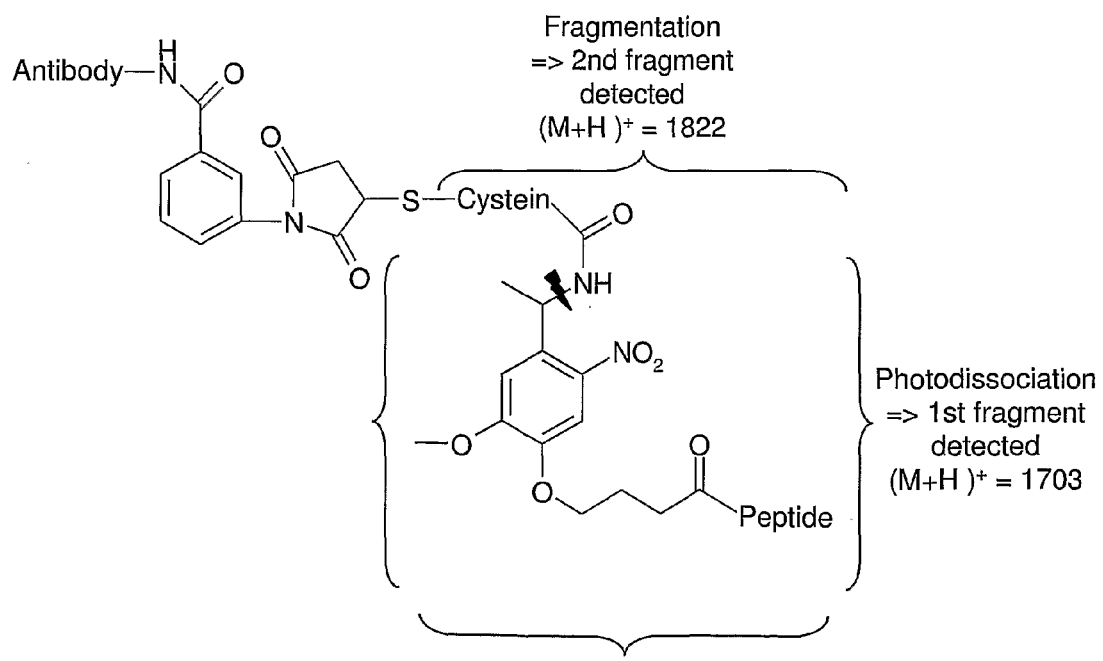
FIG. 10. Structure of an antibody-peptide conjugate with a photocleavable linker X. The 2 major fragments detected by MALDI mass spectrometry (1st fragment obtained by photo-dissociation of the Tag via cleavage of the photocleavable linker, and 2nd fragment obtained by fast fragmentation of the molecule) are shown.

The main reactions for the synthesis of the anti-body-peptide conjugate with a photocleavable linker are shown on FIG. 9. The obtained antibody-peptide conjugate has the following formula:

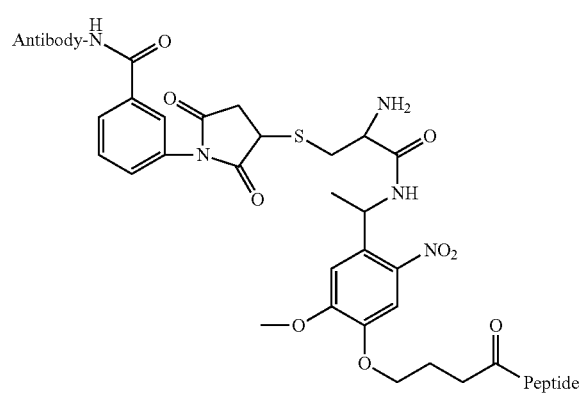

which is shown in abbreviated form in FIG. 10.

2.2 MALDI Analysis of the Obtained Antibody-Peptide Conjugate in Solution

The obtained antibody-peptide conjugate with a photocleavable linker has then been tested in solution first, to verify the ability of the tag peptide to be efficiently cleaved by photodissociation induced by the UV-MALDI laser.

The results are shown on FIG. 10, and clearly indicate that the peptide tag, still linked to the photocleavable linker PC (peptide+PC, m/z=1703), is easily detected after MALDI desorption/ionization process.

In addition, a fast fragmentation fragment comprising the tag peptide, the photocleavable linker, and a cystein initially belonging to the antibody (see FIG. 11) (peptide+PC+cystein, m/z=1822) is also detected, clearly demonstrating that the obtained antibody-peptide conjugate would also be suitable for other type of mass spectrometry (such as SIMS or DESI) analysis of a tissue section.

2.3 MALDI Direct Analysis of Rat Brain Tissue Sections Using the Obtained Antibody-Peptide Conjugate The obtained antibody-peptide conjugate with a photocleavable linker has then been tested for indirect UV-MALDI analysis of membrane protein carboxypeptidase D (180 kDa) in rat brain tissue sections.

Rat brain tissue sections were first hybridized with a primary rabbit antibody specific for carboxypeptidase D. In a second step, the antibody-peptide conjugate with a photocleavable linker was added to hybridize with primary antibodies present on the tissue section.

The resulting stained tissue sections were then analyzed using UV-MALDI.

Figure 12:
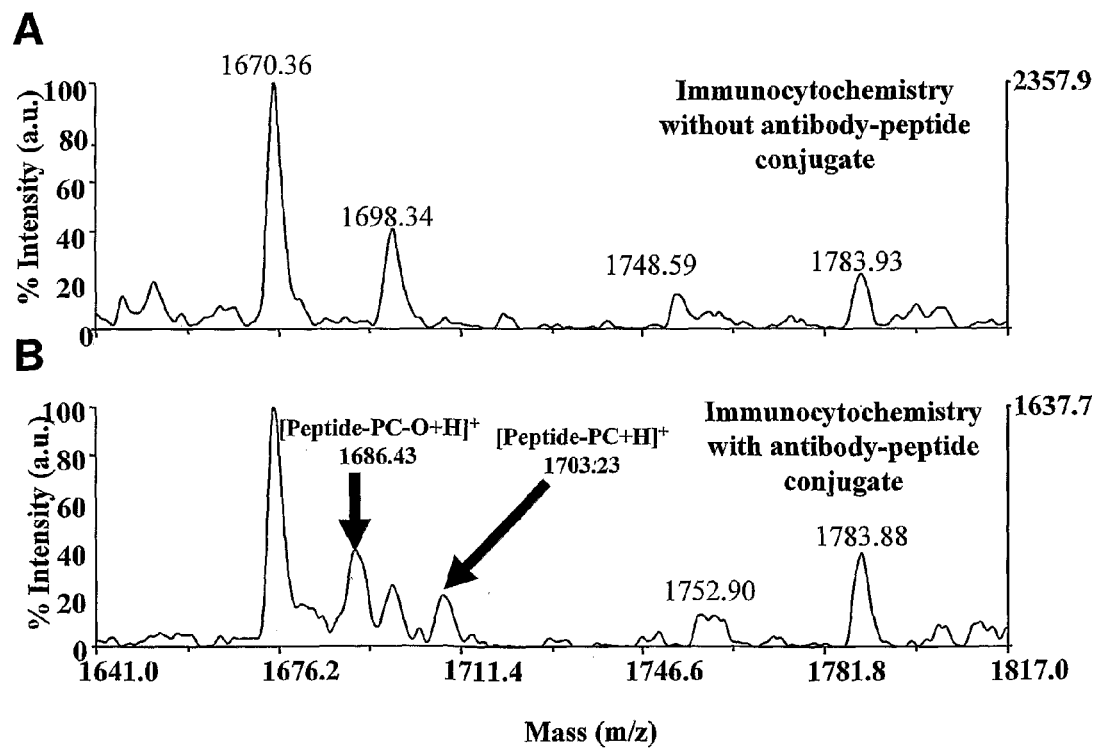
FIG. 12. Typical mass spectrum obtained during direct analysis of a rat brain tissue section using no conjugate (A, rat brain control) versus using an antibody-peptide conjugate with a photocleavable linker (B).

A typical spectrum is displayed on FIG. 12. It clearly indicates that the peptide tag, still linked to the photocleavable linker PC (peptide+PC, m/z=1703.23), is easily detected using indirect UV-MALDI tissue section analysis. Another fragment corresponding to the tag peptide (peptide+PC+O, m/z=1686.43) is also easily detected.

Figure 13:
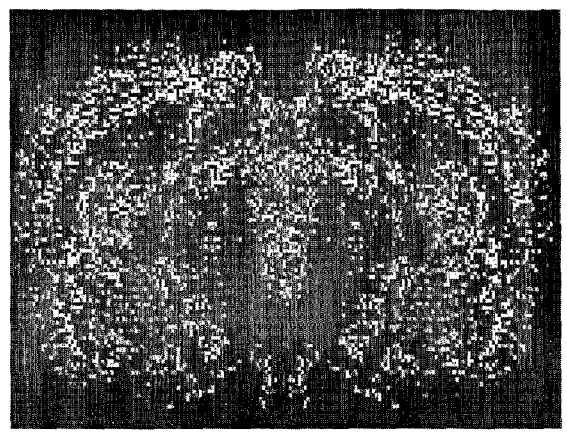
FIG. 13. Expression map of membrane protein carboxypeptidase D (180 kDa) detected with a rabbit primary antibody directed against this protein and the antibody-peptide conjugate with a photocleavable linker. The image has been reconstructed from the detection signal corresponding to the peptide tag.

Using the method according to the invention, the rat brain tissue section was scanned, each spectrum data being stored, and the image of the expression map of carboxypeptidase D was constructed. The result is displayed in FIG. 13, and clearly shows that it is possible to construct an expression map using the method according to the invention with an antibody-peptide conjugate with a photocleavable linker.

In addition, to further demonstrate the reliability of the method according to the invention to construct expression maps, the rat brain tissue section stained with rabbit primary antibodies specific for carboxypeptidase D where developed using T-chloronaphtol as chromogen after fixation on a classical commercial secondary antibody. The obtained staining colocalized with the MALDI detection of carboxypeptidase D (data not shown), thus demonstrating the reliability of the method according to the invention and MALDI imaging shows to be even more sensitive than classical revelation.

These results demonstrate that the synthesized antibody-peptide conjugate with a photocleavable linker permits the indirect detection of a protein in a tissue section, as well as the construction of an expression map.

EXAMPLE 3

Demonstration of the Possibility to Use Fast Fragmentation Instead of Photodissociation for Indirect Mass Spectrometry Analysis of Biomolecules Present in Tissue Sections Fast fragmentation is usually considered as a detrimental but inevitable phenomenon.

In the present case, the inventors have found that it is possible to take advantage of this necessary phenomenon to implement a method for determining at least one target molecule map in a tissue section using (A-X)n-B conjugates in which the linker X is cleaved by fast fragmentation.

3.1 Fast Fragmentation for Indirect Mass Spectrometry Analysis of Biomolecules Present in Tissue Sections Using Conjugates in which the Linker is Photocleavable at the Wavelength of a UV-MALDI Laser Although this concept is transposable to other mass spectrometry technologies, such as SIMS or DESI mass spectrometry, the inventors have first proven the possible use of this concept using MALDI mass spectrometry and conjugates in which the linker is photocleavable at the wavelength of a UV-MALDI laser.

Indeed, when using either oligo-peptide conjugates or antibody-peptide conjugates with photocleavable linkers (PC), in addition to expected (peptide+PC) fragments, other fragments comprising the peptide tag are observed, these fragments corresponding to fast fragmentation fragments of the conjugates.

More precisely, when using 3 distinct oligo-peptide conjugates with photocleavable linkers (see Example 1 for a more precise definition of these conjugates), fragments corresponding to the tag peptide 1, peptide 2 or peptide 3 are observed in addition to expected fragments (peptide 1, 2 or 3+PC), as is clearly shown on FIG. 4C. For instance, for conjugate 2 using a peptide 2 tag molecule, both a photodissociation fragment and a fast fragmentation fragment are observed:

expected photodissociation fragment=(peptide 2+PC), m/z=1892; and fast fragmentation fragment=peptide 2 only, m/z=1450.

The same phenomenon is observable for conjugate 3 on FIG. 4C:

expected photodissociation fragment=(peptide 3+PC), m/z=1604; and fast fragmentation fragement=peptide 3 only, m/z=1162.

Figure 11:
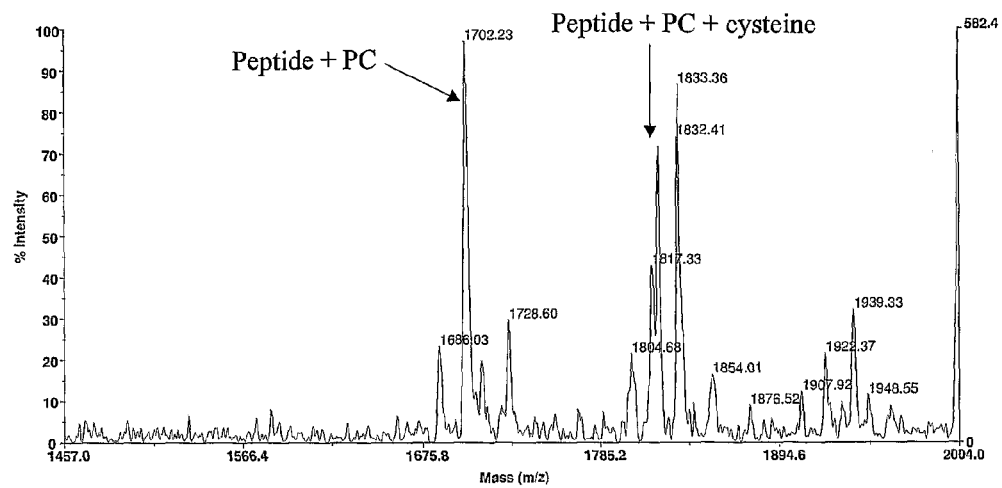
FIG. 11. Typical mass spectrum obtained during in solution MALDI analysis of an antibody-peptide conjugate with a photocleavable linker X (matrix sinapinic acid SA).

When using the antibody-peptide conjugate described in Example 2 also, both an expected photodissociation fragment and a fast fragmentation fragment are observed as shown in FIG. 11:

expected photodissociation fragment=(peptide+PC), m/z=1702; and fast fragmentation fragment=peptide+PC+cystein, m/z=1822.

3.2 Fast Fragmentation for Indirect Mass Spectrometry Analysis of Biomolecules Present in Tissue Sections Using a FITC Labelled Antibody The inventors have also analyzed the possibility to use fast fragmentation for indirect mass spectrometry analysis of biomolecules present in tissue sections using conventional, and notably commercial, labelled antibodies.

Indeed, conventional labelling molecules have definite molecular weights and may thus be used as tag molecules. In addition, all sorts of antibody, with a very wide range of antigenic specificities, are commercially available as labelled antibodies. Finally, technologies to attach a labelling molecule via conventional linkers to any antibody are well-known routine technologies, thus ensuring that the possibility to use conventionally labelled antibodies for indirect mass spectrometry analysis of biomolecules present in tissue sections would permit to significantly enlarge the number of distinct biomolecules that may be mapped using the method according to the invention.

A FITC labelled antibody has been used for in solution MALDI analysis of a FITC labelled antibody using CHCA matrix.

Figure 14:
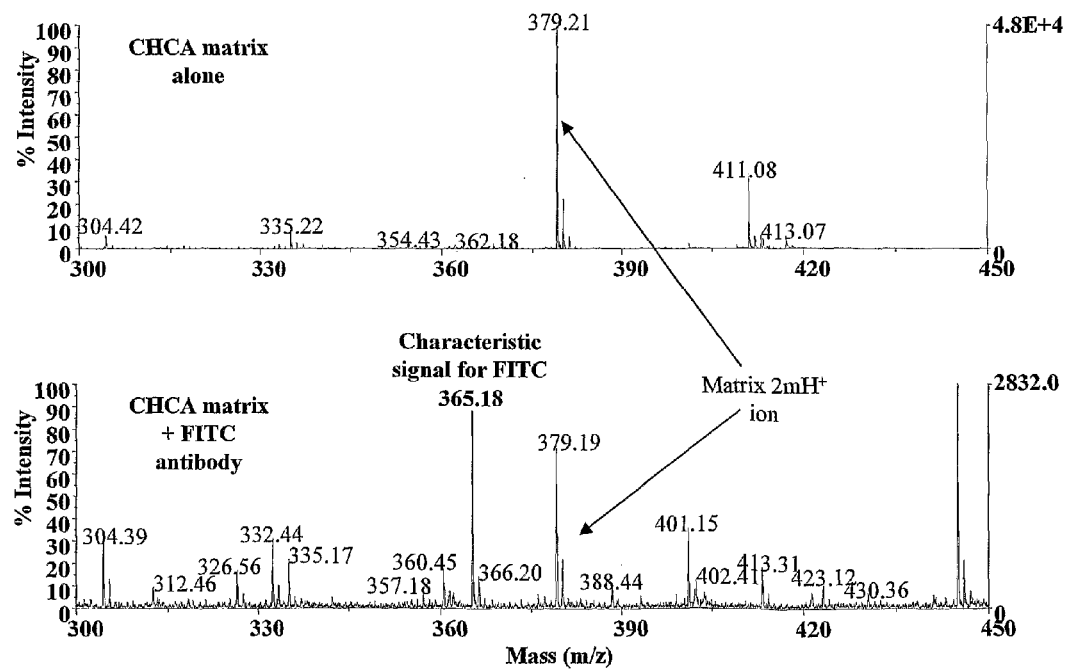
FIG. 14. Typical mass spectrum obtained during in solution MALDI analysis of a FITC labelled antibody using CHCA matrix. A. without FITC labeled antibody (CHCA matrix alone). B. with FITC labeled antibody.

Results are displayed in FIG. 14 and show that a characteristic signal for FITC molecule is easily detected (m/z=365.18). Since the linker between the antibody and the FITC molecule is not photocleavable at the MALDI laser wavelength, it clearly demonstrate that fast fragmentation permits the cleavage of the linkage between the antibody and its labelling molecule.

Although these results have yet to be confirmed on tissue section, all preceding results obtained in solution have been further confirmed on tissue sections. These results thus highly support the possibility to use fast fragmentation and conventional labelled antibodies for indirect detection of target molecules in tissue section using MALDI mass spectrometry, but also other mass spectrometry technologies involving fast fragmentation, and notably SIMS or DESI mass spectrometry.

3.3 Conclusion

The obtained results clearly demonstrate the possibility to take advantage of the usually detrimental phenomenon of fast fragmentation for the indirect detection of target molecules in tissue section using various mass spectrometry technologies, in particular MALDI, SIMS or DESI mass spectrometry.

EXAMPLE 4

Synthesis of an Antibody-Br Conjugate for Use in Mass Spectrometry Analysis of Tissue Sections Using Fragmentation to Cleave the Linker Molecule Between the Antibody and the Br Atom An antibody-Br conjugate may be synthesized using EDAC linker:

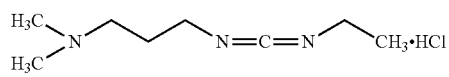

available from SIGMA under reference E1769, using the following protocol:

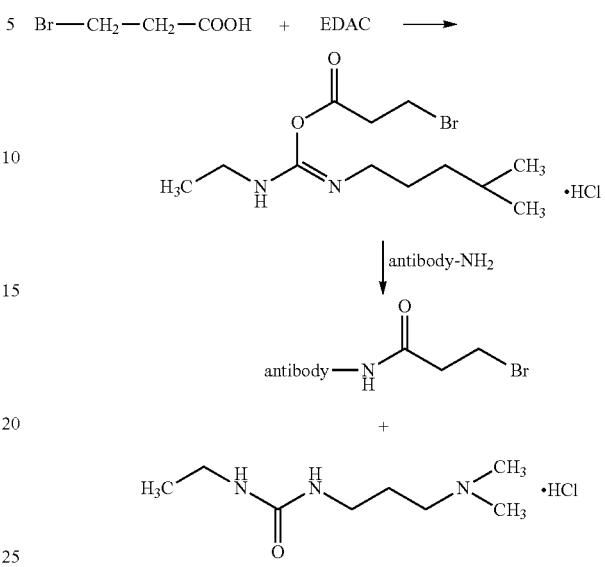

Such a protocol may be applied using any antibody or antibody fragment, to conjugate it with a Br atom. Such conjugates may be used in a method according to the invention in which fragmentation is used to cleave the linker between the antibody and the Br atom.

The invention claimed is:

1. A method for determining at least one target molecule map in a tissue section, comprising:

a) hybridizing said tissue section with at least one (A-X)-B conjugate, wherein

A is a peptide tag molecule of known molecular weight,

X is a linker that is cleaved during sample desorption/ionization,

B is an antibody binding molecule that binds specifically to said target molecule, each distinct B molecule is linked to a distinct A tag molecule, and said conjugate is of following formula:

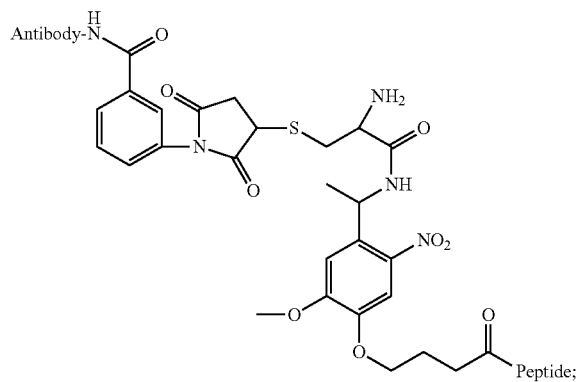

b) scanning the tissue section surface and analyzing each adjacent spot with a mass spectrometer, wherein said linker X is cleaved during sample desorption/ionization, and wherein the resulting data of each spot is saved; and c) analyzing the obtained data in the molecular mass window(s) of each distinct tag molecule to create as many maps of the tissue section as the number of distinct studied target molecules.

2. The method of claim 1, wherein at least one target molecule is a peptide, a protein, an antigen, or a hapten.

3. The method of claim 1, wherein MALDI mass spectrometry is used and the X linker molecule is photocleavable at the wavelength of a MALDI laser.

4. The method of claim 1, wherein said X linker molecule is cleaved by fragmentation during sample ionization.

5. The method of claim 4, wherein UV-MALDI, IR-MALDI, SIMS or DESI mass spectrometry is used.

6. A conjugate suitable for use in a method according to claim 1, wherein said conjugate is:

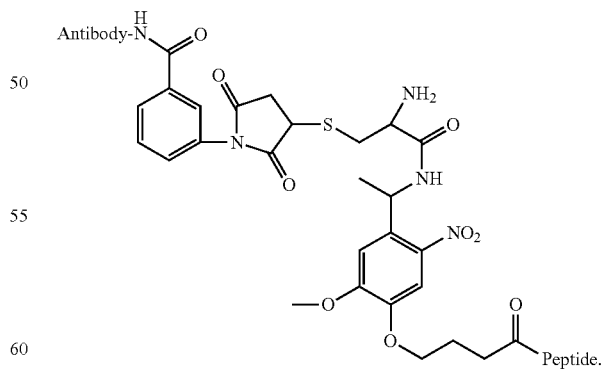

* * * * *

SEQUENCE LISTING

```
<160> NUMBER OF SEQ ID NOS: 11

<210> SEQ ID NO 1
<211> LENGTH: 9
<212> TYPE: PRT
<213> ORGANISM: Artificial Sequence
<220> FEATURE:
<223> OTHER INFORMATION: Description of Artificial Sequence: Synthetic
      Tag peptide of oligo-peptide 1

<400> SEQUENCE: 1

Gly Arg Ala Leu Gly Val Phe Val Cys
1               5

<210> SEQ ID NO 2
<211> LENGTH: 12
<212> TYPE: PRT
<213> ORGANISM: Artificial Sequence
<220> FEATURE:
<223> OTHER INFORMATION: Description of Artificial Sequence: Synthetic
      Tag peptide of oligo-peptide 2

<400> SEQUENCE: 2

Arg Pro Lys Pro Gln Gln Phe Phe Gly Leu Met Cys
1               5                   10

<210> SEQ ID NO 3
<211> LENGTH: 10
<212> TYPE: PRT
<213> ORGANISM: Artificial Sequence
<220> FEATURE:
<223> OTHER INFORMATION: Description of Artificial Sequence: Synthetic
      Tag peptide of oligo-peptide 3
```

```
<400> SEQUENCE: 3

Arg Pro Pro Gly Phe Ser Pro Phe Arg Cys
1               5                   10

<210> SEQ ID NO 4
<211> LENGTH: 10
<212> TYPE: PRT
<213> ORGANISM: Artificial Sequence
<220> FEATURE:
<223> OTHER INFORMATION: Description of Artificial Sequence: Synthetic
      Tag peptide of oligo-peptide Forward

<400> SEQUENCE: 4

Arg Pro Pro Gly Phe Ser Pro Phe Arg Cys
1               5                   10

<210> SEQ ID NO 5
<211> LENGTH: 10
<212> TYPE: PRT
<213> ORGANISM: Artificial Sequence
<220> FEATURE:
<223> OTHER INFORMATION: Description of Artificial Sequence: Synthetic
      Tag peptide of oligo-peptide Reverse

<400> SEQUENCE: 5

Arg Pro Pro Gly Phe Ser Pro Phe Arg Cys
1               5                   10

<210> SEQ ID NO 6
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide of oligo-peptide 1

<400> SEQUENCE: 6
cacgtacagg atgtacag                                              18

<210> SEQ ID NO 7
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide of oligo-peptide 2

<400> SEQUENCE: 7
tcgagaggta catcgtg                                               17

<210> SEQ ID NO 8
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide of oligo-peptide 3

<400> SEQUENCE: 8
aagcggtacg agtagca                                               17

<210> SEQ ID NO 9
<211> LENGTH: 25
<212> TYPE: DNA
<213> ORGANISM: Artificial Sequence
<220> FEATURE:
<223> OTHER INFORMATION: Description of Artificial Sequence: Synthetic
```

```
            oligonucleotide of oligo-peptide Forward

<400> SEQUENCE: 9
gacgtaccag gcggtagctg cattt                                    25

<210> SEQ ID NO 10
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide of oligo-peptide Reverse

<400> SEQUENCE: 10
caggactccc caaaggagaa cagga                                    25

<210> SEQ ID NO 11
<211> LENGTH: 13
<212> TYPE: PRT
<213> ORGANISM: Artificial Sequence
<220> FEATURE:
<223> OTHER INFORMATION: Description of Artificial Sequence: Synthetic
      Tag peptide of antibody-peptide conjugate

<400> SEQUENCE: 11

Asp Ser Pro Glu Gly Leu Asn Arg Lys Gln Lys Pro Ala
1               5                   10
```